(12) United States Patent
Raduchel et al.

(10) Patent No.: US 10,601,960 B2
(45) Date of Patent: *Mar. 24, 2020

(54) ZERO-KNOWLEDGE ENVIRONMENT BASED NETWORKING ENGINE

(71) Applicant: eIngot LLC, Great Falls, VA (US)

(72) Inventors: William J. Raduchel, Palo Alto, CA (US); Art Spivy, Great Falls, VA (US)

(73) Assignee: eIngot LLC, Great Falls, VA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/896,347

(22) Filed: Feb. 14, 2018

(65) Prior Publication Data

US 2019/0253523 A1  Aug. 15, 2019

(51) Int. Cl.
| | |
|---|---|
| *H04L 29/06* | (2006.01) |
| *H04L 29/08* | (2006.01) |
| *G06Q 50/00* | (2012.01) |
| *G06F 21/62* | (2013.01) |
| *H04L 9/06* | (2006.01) |
| *G06F 9/455* | (2018.01) |
| *H04W 4/21* | (2018.01) |

(52) U.S. Cl.
CPC .......... *H04L 67/42* (2013.01); *G06F 9/45558* (2013.01); *G06F 21/6218* (2013.01); *G06Q 50/01* (2013.01); *H04L 9/0637* (2013.01); *H04L 63/0428* (2013.01); *H04L 63/062* (2013.01); *H04L 63/08* (2013.01); *H04L 63/102* (2013.01); *H04L 63/12* (2013.01); *H04L 67/12* (2013.01); *H04L 67/306* (2013.01); *H04W 4/21* (2018.02); *G06F 2009/45595* (2013.01); *H04L 2209/38* (2013.01)

(58) Field of Classification Search
CPC ..... G16H 10/60; G06F 21/6245; G06F 21/31; G06F 21/33; G06F 21/6272; G06F 19/321; G06F 19/30; G06F 17/30011; G06F 17/30312; G06F 21/6227; G06Q 50/24

See application file for complete search history.

(56) References Cited

U.S. PATENT DOCUMENTS

| | | |
|---|---|---|
| 5,995,943 A | 11/1999 | Bull et al. |
| 6,338,039 B1 | 1/2002 | Lonski et al. |

(Continued)

FOREIGN PATENT DOCUMENTS

| | | |
|---|---|---|
| CN | 1650305 | 8/2005 |

OTHER PUBLICATIONS

Turnbull "The Docker Book" Aug. 4, 2014, v1.0.7 (Year: 2014).*

(Continued)

*Primary Examiner* — Hitesh Patel
(74) *Attorney, Agent, or Firm* — Fish & Richardson P.C.

(57) ABSTRACT

Methods, systems, and apparatus are described providing networking engines. Specifically, a method for implementing software containers implementing network engines that may be configured to act in a zero-knowledge environment is described. All information pertaining to the network engine associated with a user that is stored in the container is solely that of a user unless explicitly shared by the user. The containers may be configured to participate in a publish-and-subscribe network in order to share information. In addition, the containers may be provisioned with controls so that global operators may comply with local privacy rules.

18 Claims, 16 Drawing Sheets

(56) References Cited

U.S. PATENT DOCUMENTS

| | | | |
|---|---|---|---|
| 6,463,417 B1 | 10/2002 | Schoenberg | |
| 6,845,448 B1 | 1/2005 | Chaganti et al. | |
| 6,988,075 B1 | 1/2006 | Hacker | |
| 7,466,235 B1 | 12/2008 | Kolb et al. | |
| 7,617,114 B1 | 11/2009 | Tooke, III | |
| 8,600,776 B2 | 12/2013 | Raduchel | |
| 8,955,102 B1* | 2/2015 | Harding | G06F 21/6245 726/21 |
| 9,686,356 B2 | 6/2017 | Raduchel | |
| 10,044,507 B2 | 8/2018 | Raduchel | |
| 2002/0010679 A1 | 1/2002 | Felsher | |
| 2002/0013517 A1 | 1/2002 | West et al. | |
| 2002/0016821 A1 | 2/2002 | Son et al. | |
| 2002/0042725 A1 | 4/2002 | Mayaud | |
| 2002/0042884 A1 | 4/2002 | Wu et al. | |
| 2003/0074248 A1 | 4/2003 | Braud et al. | |
| 2003/0140044 A1 | 7/2003 | Mok et al. | |
| 2003/0191669 A1 | 10/2003 | Fitzgerald | |
| 2003/0195774 A1 | 10/2003 | Abbo | |
| 2003/0233342 A1 | 12/2003 | Vadrot | |
| 2004/0148194 A1 | 7/2004 | Wellons | |
| 2004/0260577 A1 | 12/2004 | Dahlin et al. | |
| 2006/0106836 A1 | 5/2006 | Masugi et al. | |
| 2007/0027721 A1 | 2/2007 | Hasan et al. | |
| 2007/0061170 A1 | 3/2007 | Lorsch | |
| 2007/0078677 A1 | 4/2007 | Hofstetter | |
| 2007/0138253 A1 | 6/2007 | Libin et al. | |
| 2008/0009344 A1 | 1/2008 | Graham et al. | |
| 2008/0109651 A1 | 5/2008 | Duda et al. | |
| 2008/0177569 A1 | 7/2008 | Chen et al. | |
| 2009/0012817 A1 | 1/2009 | Squires et al. | |
| 2009/0037224 A1 | 2/2009 | Raduchel | |
| 2009/0044259 A1 | 2/2009 | Bookman et al. | |
| 2011/0085667 A1* | 4/2011 | Berrios | G06F 21/445 380/282 |
| 2011/0161172 A1 | 6/2011 | Lee | |
| 2011/0208559 A1 | 8/2011 | Fontoura | |
| 2011/0258441 A1 | 10/2011 | Ashok | |
| 2012/0042000 A1* | 2/2012 | Heins | G06Q 10/10 709/201 |
| 2012/0078660 A1 | 3/2012 | Mangicaro et al. | |
| 2012/0089678 A1* | 4/2012 | Cort | G06Q 50/01 709/204 |
| 2012/0123798 A1 | 5/2012 | Lanzalotti | |
| 2013/0018855 A1 | 1/2013 | Eshghi et al. | |
| 2013/0205022 A1 | 8/2013 | Kagan et al. | |
| 2013/0268284 A1 | 10/2013 | Heck | |
| 2013/0346518 A1 | 12/2013 | Soundararajan | |
| 2014/0081669 A1 | 3/2014 | Raduchel | |
| 2014/0095286 A1* | 4/2014 | Drewry | G06Q 30/02 705/14.26 |
| 2014/0095319 A1 | 4/2014 | Bruns et al. | |
| 2014/0310063 A1 | 10/2014 | Freeman | |
| 2014/0372748 A1 | 12/2014 | Dixon | |
| 2015/0142986 A1 | 5/2015 | Reznik | |
| 2016/0063215 A1* | 3/2016 | Zamer | G06F 19/3481 705/3 |
| 2016/0292370 A1 | 10/2016 | Saric | |
| 2017/0032092 A1 | 2/2017 | Mink | |
| 2018/0039737 A1* | 2/2018 | Dempers | G06F 21/6245 |
| 2019/0208354 A1 | 7/2019 | Raduchel | |
| 2019/0287663 A1 | 9/2019 | Raduchel | |

OTHER PUBLICATIONS

Kemoni, "The Impact of Records Centres on the Management of Public Sector Records in Kenya," dated Apr. 1998, 13 pages.

Indian Office Action in Indian Application No. 8383/DELNP/2009, dated Jun. 22, 2018, 8 pages.

Baig, Edward C., "Amazon exec: Alexa should be able to talk to Siri," USA Today, Jun. 7, 2017, URL <https://www.usatoday.com/story/tech/columnist/baig/2017/06/07/amazons-exec-alexa-should-able-talk-siri/102594930/>.

Chinese Notification of the First Office Action (with English translation) for Application No. 200880022802.5 dated May 24, 2011, 9 pages.

Chinese Notification of the Office Action issued in CN201210112416.3 dated Sep. 22, 2014, with English Translation, 20 pages.

European Extended Search Report in European Application No. 15831680.2, dated Mar. 5, 2018, 6 pages.

International Preliminary Report on Patentability in International Application No. PCT/US2015/056961, dated Apr. 25, 2017, 12 pages.

International Search Report and Written Opinion in International Application No. PCT/US2018/018507, dated Mar. 12, 2018, 12 pages.

International Search Report and Written Opinion in International Application No. PCT/US2015/044887, dated Mar. 3, 2016, 16 pages.

International Search Report and Written Opinion in International Application No. PCT/US15/56961, dated Jan. 11, 2016, 12 pages.

Lujo Bauer, Cristian Bravo-Lillo, Elli Fragkaki, and William Melicher. 2013. A Comparison of users' perceptions of and willingness to use Google, Facebook, and Google+ single-sign-on functionality. In Proceedings of the 2013 ACM workshop on Digital identity management *DIM '13). ACM, New York, NY, USA 25-36.

M.J. Scheepers, "Virtualization and Containerization of Application Infrastructure: A Comparison," 2014, University of Twente.

PCT Notification Concerning Transmittal of International Preliminary Report on Patentability for Application No. PCT/US2008/069228 dated Sep. 10, 2008, 11 pages.

PCT Notification of Transmittal of the International Search Report and the Written Opinion for Application No. PCT/US08/69228 dated Sep. 10, 2008, 15 pages.

Roseberry, Can Any Bluetooth Enabled Cell Phone Be Used as a Modem?, Jul. 23, 2006, /mobileoffice.about.com/od/usingyourphone/f/bluetoothphones.htm>.

Turnbill, James, "The Docker Book", Aug. 4, 2014, The Docker Book v1.0.7 (8f1618c), p. 1-280.

U. Feige, A. Fiat and A. Shamir, "Zero-knowledge proofs of identity", J. Cryptology, vol. 1, pp. 77-94, 1988.

U.S. Final Office Action for U.S. Appl. No. 12/167,746 dated May 5, 2011, 10 pages.

U.S. Final Office Action for U.S. Appl. No. 14/083,691 dated Mar. 30, 2015, 12 pages.

U.S. Final Office action for U.S. Appl. No. 14/083,691 dated Mar. 24, 2016, 16 pages.

U.S. Final Office Action for U.S. Appl. No. 14/824,828 dated Jun. 9, 2016, 24 pages.

U.S. Non-Final Office Action for U.S. Appl. No. 12/167,746 dated Oct. 12, 2010, 12 pages.

U.S. Non-Final Office Action for U.S. Appl. No. 14/083,691 dated Mar. 27, 2014, 13 pages.

U.S. Non-Final Office Action for U.S. Appl. No. 14/083,691 dated Jul. 17, 2015, 10 pages.

U.S. Non-Final Office Action for U.S. Appl. No. 14/083,691 dated Oct. 23, 2014, 16 pages.

U.S. Non-Final Office Action for U.S. Appl. No. 14/523,110, dated Jul. 8, 2016, 14 pages.

U.S. Non-Final Office Action for U.S. Appl. No. 14/824,828 dated Dec. 3, 2015, 21 pages.

U.S. Non-Final Office Action for U.S. Appl. No. 15/435,150, dated Feb. 26, 2018, 18 pages.

U.S. Notice of Allowance for U.S. Appl. No. 12/167,746 dated Jul. 29, 2013, 13 pages.

U.S. Notice of Allowance for U.S. Appl. No. 14/083,691, dated Jun. 17, 2016, 11 pages.

U.S. Office Action for U.S. Appl. No. 15/435,150, dated Feb. 26, 2018, 18 pages.

Baig, Edward C., "Amazon exec: Alexa should be able to talk to Siri," USA Today, Jun. 7, 2017, URL<https://www.usatoday.com/story/tech/colunmnist/baig/2017/06/07/amazons-exec-alexa-should-able-talk-siri/102594930/>.

Office Action issued in CN201210112416.3 dated Sep. 22, 2014, with English Translation, 20 pages.

(56) References Cited

OTHER PUBLICATIONS

U. Feige, A. Fiat and A. Shamir, "Zero-knowledge proofs of identity", J. Ctyptology, vol. 1, pp. 77-94, 1988.
U.S. Non-Final Office Action for U.S. Appl. No. 16/432,382, dated Jul. 8, 2019, 27 pages.
PCT Notification Concerning Transmittal of International Preliminary Report on Patentability for Application No. PCT/US2018/018507, dated Aug. 29, 2019, 10 pages.
Batz et al., "P2P applied in CMS for advertising," 2009 Fourth International Conference on Digital Information Management, 2009, 1-8.
Neng-Wen Wang, Yueh-Min Huang, "A novel software key container in on-line media services," Computers & Electrical Engineering, 2009, 35(2):370-5.
Office Action issue in U.S. Appl. No. 14/824,828 dated Dec. 3, 2015, 21 pages.
Office Action issued in U.S. Appl. No. 14/824,828 dated Jun. 9, 2016, 24 pages.

* cited by examiner

500

| | | Container Manager | |
| | | 521 | |
| Container ID | IP Address | Service Level | Supplemental Applications |
| 00 | .123 | A | 2 |
| 01 | .124 | B | 3 |
| 02 | .125 | C | 10 |

| Service Level | Cycles | Main Memory | Bandwidth | Second Tier Storage |
|---|---|---|---|---|
| A | 100 PUC | 2 GB | 10X | 1TB |
| B | 10 PUC | 20 MB | 2X | 2GB |
| C | 1 PUC | 10 MB | .01X | 1GB |

```
                    Social Network Administration Tool
                                    703

User ID   Social Network   Av. Bandwidth   Primary Container ID   Primary Device ID
   A         Facebook         500 MB                00                    AA
   B         LinkedIn         200 MB                01                    BB
   C         Twitter           0 MB                 02                    CC Backup Device ID
                                                                         BB
                                                                         CC
                                                                         AA
```

| | | Container Administration Tool | | |
|---|---|---|---|---|
| | | 804 | | |
| Container ID | IP Address | Social Network | User | Interface Type |
| 00 | .123 | Facebook | A | Public |
| 01 | .124 | LinkedIn | B | Public |
| 02 | .126 | Man UTD Fan | C | Private |

| Container ID | Primary Device ID | Backup Device ID |
|---|---|---|
| 00 | AA | BB |
| 01 | BB | CC |
| 02 | CC | AA |

| Manchester United Fan Forum 902 | |
|---|---|
| List of members | IP Address |
| Legion_of_Rooney | X.Y.Z.A |
| Alex_Ferguson | X.Y.Z.B |
| Publish Security Configuration | |
| Allow Discovery | Yes |
| Maintain Active Sockets | Yes |
| Period of Pulling | 2 minutes |
| Allow Constituent Applications ? | |
|     Messaging ? | Yes |
|     Undefined ? | No |

```
┌─────────────────────────────────────┐
│ Receive first location data         │
│ indicating a location of            │
│ a user                              │
│                            1502     │
└─────────────────────────────────────┘
              │
              ▼
┌─────────────────────────────────────┐
│ Access second location data         │
│ indicating locations                │
│ of one or more other users          │
│                            1504     │
└─────────────────────────────────────┘
              │
              ▼
┌─────────────────────────────────────┐
│ Determine that the location of      │
│ the user corresponds to a location  │
│ of a particular other user          │
│                            1506     │
└─────────────────────────────────────┘
              │
              ▼
┌─────────────────────────────────────┐
│ Calculate an updated score,         │
│ priority, or outcome probability    │
│                            1508     │
└─────────────────────────────────────┘
              │
              ▼
┌─────────────────────────────────────┐
│ Transmit at least one of an alert,  │
│ network data, or a recommendation   │
│                            1510     │
└─────────────────────────────────────┘
              │
              ▼
┌─────────────────────────────────────┐
│ Transmit authentication information │
│ for the at least one of the alert,  │
│ network data, or recommendation     │
│                            1512     │
└─────────────────────────────────────┘
```

FIG. 15

ZERO-KNOWLEDGE ENVIRONMENT BASED NETWORKING ENGINE

FIELD

This disclosure relates generally to networking engines.

OVERVIEW

A significant challenge facing current one-to-many information sharing platforms such as social networks, are public policy concerns over privacy laws that trouble a great many users because the social network administrators currently have the potential for tremendous visibility into messages, profiles, and demographics for a user community without explicit permission from any particular user in the user community. Social network security and privacy issues result from the large amounts of information that one-to-many information sharing platforms process each day. Features that invite users to participation—messages, invitations, photos, open platform applications and other applications often reveal a user's private information. All of this has led to concerns that users are providing far too much information on social networking sites which may have serious implications on their privacy.

An additional challenge facing social networks is the computational complexity and cost to scale to global-sized Internet audiences. As additional feature sets and analytics are being added into a content-suggestion engine, the per-user computational burden may make administration of social networks more expensive. As the size of a social network grows, the burden of identifying matching and responsive content may prove problematic as the number of cycles required to promote, identify, and/or suggest a news item may grow to unsustainable levels as more social connections must be analyzed.

Accordingly, a user or a community may desire one-to-many information sharing platforms that does not involve giving up privacy information to administrators or vendors that implement such information sharing platforms. Additionally, a need also exists for implementing social networking networks that can attend to the need of global-sized Internet audiences and are inexpensive, computationally undemanding and does not compromise user privacy.

Platforms that share information may also include health networks where health network data regarding patients may be shared with health care providers and other care stakeholders, such as family caregivers, social workers, etc. Similar challenges faced in social networks described above may also be faced in health networks. For example, a patient may desire to give a first doctor access to only a portion of their heath network data, give a second doctor access to a different portion of their health network data, and give a third doctor access to all of their health network data.

BRIEF DESCRIPTION OF THE DRAWINGS

FIG. 5 is a screenshot of an instance of a graphical user interface (GUI) of a container manager that can manage different containers.

FIG. 7 is a screenshot of an instance of a graphical user interface (GUI) for a social network administration tool 703.

FIG. 8 is a screenshot of an instance of a graphical user interface (GUI) for a container administration tool.

FIG. 9 is a screenshot of an instance of a graphical user interface (GUI) for a social network associated with a Manchester United Fan Forum.

FIG. 15 is a process performed by a system that can provide analyzing user network data. Like reference numbers and designations in the various drawings indicate like elements.

DETAILED DESCRIPTION

Figure 1:
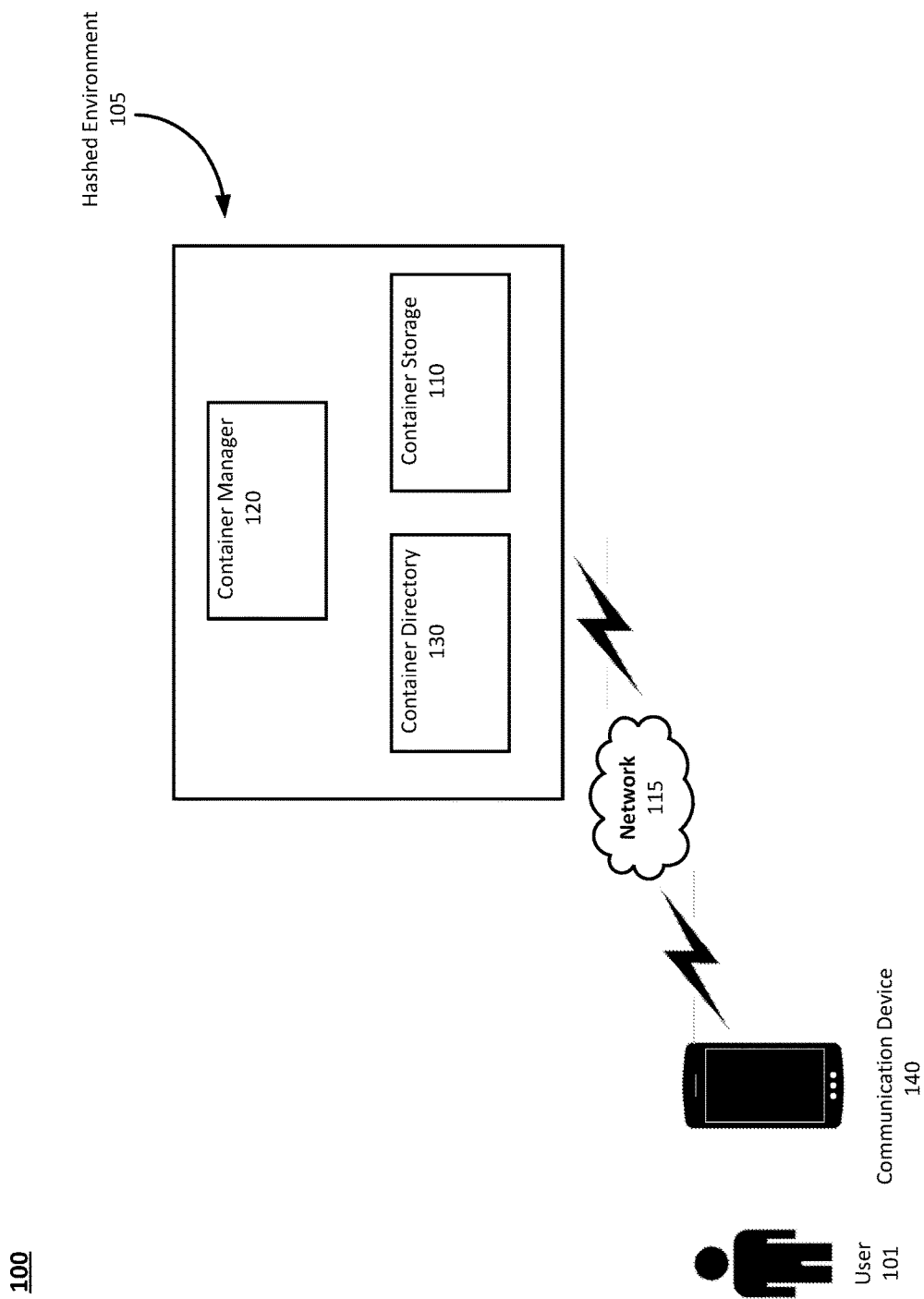
FIG. 1 is a system block diagram of an example system that can provide a zero-knowledge environment for social networking based on containers.

Currently, different one-to-many information sharing platforms such as various social networking sites vary in the levels of privacy offered to users. For some social networking sites like Facebook, providing real names and other personal information is encouraged by the site (onto a page known as a 'Profile'). These information usually consist of birth date, current address, and telephone number(s). Some sites also allow users to provide more information about themselves such as interests, hobbies, favorite books or films, and even relationship status. However, there are other social network sites, such as Match.com, where most people prefer to be anonymous. Thus, linking users to their real identity can sometimes be rather difficult. Nevertheless, individuals can sometimes be identified with face re-identification. Studies have shown that by overlapping similar photographs and profile pictures on one website with similar pictures over multiple sites 15% of the users of a website can be identified.

Social network security and privacy issues result from the large amounts of information these sites process each day. Features that invite users to increase participation—messages, invitations, photos, open platform applications and other applications are often the avenues for others to gain access to a user's private information. It is possible for users to block other users from locating them on different social networking sites like Facebook, but this must typically be done by individual basis, and is therefore not commonly used for a wide number of people. Many users do not realize that while they make use of the security features on Facebook, the default setting is restored after each update. All of this has led to many concerns that users are displaying far too much information on social networking sites, which may have serious implications on their privacy.

Modern day advances in data center technology can allow for hosted applications in environments where users and user communities can import their applications to a broader infrastructure. Such advances can allow a social network to be implemented in a zero-knowledge environment, e.g., in a container, where the hosting entity does not have access to the data associated with a user that is stored in the container. In the current specification, methods, systems, and apparatus are described for implementing one-to-many information sharing platforms, e.g., social networks, in a zero-knowledge environment. Specifically, the present specification relates to a method for using software containers to implement social networks that may be configured to act in a zero-knowledge environment. In such implementations, all information pertaining to the social network associated with a user that is stored in the container is solely that of a user unless explicitly shared by the user. In some implementations, the containers may be configured to participate in a publish-and-subscribe network in order to share information. In addition, the containers may be provisioned with controls so that global operators may comply with local privacy rules.

In one configuration, a social network is implemented in which every active person has a dedicated software environment running in a secure sandbox, such as a Linux-based container. The container can be controlled by parameters to enable personalization so that in principle one container can serve all instances across multiple environments and interfaces. However, in other circumstances, local laws, testing and migration may require the use of multiple containers.

Docker may be employed to implement such personal containers. Docker itself relates to an open-source project that automates the deployment of applications inside software containers. Widespread support for Docker allows such containers to be operated across a wide range of environments both in the cloud, locally or hosted. Docker may provide an additional layer of abstraction and automation of operating system-level virtualization, for example, on Linux. Docker uses resource isolation features of the Linux kernel such as cgroups and kernel namespaces to allow independent "containers" to run within a single Linux instance, avoiding overhead associated with starting virtual machines.

In order to realize this level of abstraction, a Linux kernel's namespaces may be employed to isolate an application's view of the operating environment, including process trees, network, user IDs and mounted file systems, while additional structures (e.g., cgroups) provide resource isolation, including the CPU, memory, block I/O and network. A library (e.g., libcontainer) may directly use virtualization facilities provided by the Linux kernel, in addition to using abstracted virtualization interfaces.

In some implementations, a user may elect to include services within the container that operate on its information (or data) to request and display other information, such as advertisements, appropriate for the user without disclosing the information used to target such advertisements to anyone else (e.g., other users, hosting entity, etc.). In another example of a service within a container, a user may elect to include a population health service to analyze the user's health network data. This population health service would analyze the user's health network data to identify the user's potential health risks and complications. A key advantage of this approach is the user's health network data can be analyzed without exposing the data to companies or services performing the population health services. Hence, other users will not have access to the data stored in the container that is associated with the user unless the user explicitly allows sharing of either portions of or the entirety of the data associated with the user with the other users. This environment is known as a zero-knowledge environment where all the data or information stored in a container associated with a user is solely related to the user. The user can also have the capability to control, customize and operate the container from any communication device such as a desktop computer, a laptop computer, a tablet, a smart phone, etc. In some implementations, the users can use the data stored in the container to create new public social network(s), create private social network(s), participate in existing advanced social network(s), etc.

In some implementations, a personal container may be configured to include advertising. However, the advertising service can operate without sharing any information other than the advertisement selected conforming to a zero-knowledge environment.

A social media architecture may be configured to operate using a publish-and-subscribe system where an identity controls one or more processes that self-administer the identity-specific permissions based on the user's preferences. For example, a social networking community may be built around containers (such as Docker or a similar technology) associated with a particular address (e.g., an IPv6 address or unique Domain Name System address). Each running container may be metered to allow a specified amount of processing power and may facilitate encrypted communications between the user device and the server-side virtual machine processes. In addition, the data for each container may be encrypted to prevent unauthorized use.

In one configuration, a container (e.g., a software container) is an operating system-level virtualization or a server virtualization method where the kernel of an operating system allows for multiple isolated user space instances, instead of just one. Such instances (often called containers, virtualization engines (VE), virtual private servers (VPS), or jails) may look and feel like a real server from the point of view of its owners and users. Virtual hosting environments commonly use operating system-level virtualization (i.e., software containers), where it is useful for securely allocating finite hardware resources amongst a large number of mutually-distrusting users. System administrators or network administrators may also use it, to a lesser extent, for consolidating server hardware by moving services on separate hosts into containers on the one server.

A container may be configured to operate in environments where privacy is desired or required by law. In some instances, regulations in various countries, such as the Health Insurance Portability and Accountability Act of 1996 (HIPAA) in the U.S., restrict covered entities from disclosing protected health information ("PHI"). The disclosure of PHI is regulated because it is healthcare data with personally identifiable information ("PII"). Many data sources would be considered covered entities because the data sources produce information that may contain PHI, and PHI through its associated Pll can be used to positively identify the patient with whom the healthcare data is related. In some implementations, a hospital may offer a social network during a patient's visit where the social network is accessed to coordinate medical care in a manner where patient privacy is mandated by law (e.g., HIPAA). In such implementations, the containers (or virtual machines) used by the hospital to execute the social network may be configured to remove personally identifiable information and instead transmit only labels that anonymously identify the patient.

Examples of the potential dangers to a user that can result from unintended loss of privacy information can include: (i) identity theft—loss of personal information such as a user's social security number or date of birth can lead to malicious impersonation of a user for making nefarious credit card applications, purchases, mortgage loan applications, airline ticket purchases, etc.; (ii) sexual predators—due to the high content of personal information placed on social networking sites, as well as the ability of a user to hide behind a pseudo-identity, such sites have become increasingly popular for sexual predators; (iii) stalking—the potential ability for stalking users on social networking sites has been noted. Popular social networking sites make it easy to build a web of friends and acquaintances, and share with them a user's photos, whereabouts, contact information, and interests without ever having the user actually meet many of their friends/acquaintances. With the amount of information that users post about themselves online, it is easy for users to become a victim of stalking without even being aware of the risk; (iv) employment—issues relating to privacy and employment are becoming a concern with regards to social networking sites. As of recently, it has been estimated that approximately one in five employers search social networking sites in order to screen potential candidates. For the majority of employers, such action is to acquire negative information about candidates. It is expected that employers will continue to use social networking sites as a means of monitoring staff and screening potential candidates, and it has been noted that such actions may be illegal under in certain jurisdictions; (v) online victimization—social networks are designed for individuals to socially interact with other people over the Internet. However, some individuals engage in undesirable online social behaviors creating negative impacts on other people's online experiences. It has created a wide range of online interpersonal victimization including sexual advances and harassments; (vii) surveillance—while the concept of a worldwide communicative network seems to adhere to the public sphere model, market forces control access to such a resource. For example, a recent investigation found that many of the applications on Facebook were transmitting identifying information about users and their friends to data aggregators such as, advertisers and internet tracking companies, which is a violation of Facebook's privacy policy; (viii) discrimination—sharing of sensitive health data with a company could lead to discrimination in keeping a job or advancing in a career. This is because every online move by a user leaves cyber footprints that are rapidly becoming fodder for research without the user's knowledge.

In some implementations, a social network provider may facilitate use of containers in order to join a social network. Upon registering and signing up with a social network, the social network provider may equip the registering user to establish required relationships with a cloud provider that can execute such a container. The containers may be configured to accept permissions from a user and may be configured to operate upon and manipulate an encrypted data set. Once installed on the user's behalf, the user then may manipulate and control the remote container. The remote containers may be configured so that performance may be regulated (permissions, memory size, computing cycles). Personally-identifiable information is controlled by the user and shared only as the user directs. The containers may be migrated or moved depending on device or virtual machine load, social network computational burden (e.g., number of interconnections), changing security requirements (e.g., receiving a security alert or indication of compromise or suspicious activity), or logical requirement (e.g., a desire to configure or develop another instantiation of a new social network or social subnetwork (interest community)).

In the context of a social networking application, "friendship" or a user-approved degree of trust between users begins by with two users mutually agreeing to share encryption keys so each can read the other's information. The respective keys for peers (fellow users) may be stored in an encrypted environment. Each running environment may be signed with the associated key so that the access device can trust the running environment. The container itself may be signed and certified as being secure. In some legal jurisdictions, an access "backdoor" or wiretapping interface may be required and employed to comply with applicable wiretapping provisions to ensure that law enforcement and other authorized users have access to desired information. In these configurations, the user would have to trust the code associated with the wiretap. One advantage of container-based social network is that the constituent components are self-contained so information entering or leaving the environment can be secured and/or tracked.

FIG. 1 is a system block diagram of an example system 100 that can provide a zero-knowledge environment for social networking based on containers. The system 100 includes a hashed environment 105 that is composed of a container storage 110, container manager 120, and a container directory 130. The hashed environment 105 is operably coupled to a communication device 140 associated with a user 101 via a network 110. The network 115 can be any type of network (e.g., a local area network (LAN), a wide area network (WAN), a virtual network, and a telecommunications network) implemented as a wired network and/or a wireless network. As described in further detail herein, in some configurations, for example, the communication device 140 can be connected to the hashed environment 105 via network 115 that can include an intranet, an Internet Service Provider (ISP) and the Internet, a cellular network (e.g., network 115), and/or the like.

The communication device 140 can be any communication device such as, for example, a desktop computer, a laptop computer, a personal digital assistant (PDA), a standard mobile telephone, a tablet personal computer (PC), and/or so forth. The communication device 140 can be used by a user 101 to set up one or multiple social networking accounts such as, for example, a Facebook account, a LinkedIn account, a Google+ account, a Twitter account, a Snapchat account, and Xbox1 account, and/or the like. The user 101 can also use the communication device 140 to communicate and/or exchange information (i.e., data) with a set of other users for personal and professional development purposes.

The hashed environment 105 is associated with (software) containers and includes a container storage 110, container manager 120, and a container directory 130. The hashed environment 105 is associated with storing and managing user data associated with one or multiple users in a (software) container. The container storage 110 can be allocated with a specified amount of storage space (e.g., 200 GB, 500 GB, 1 TB, etc.) and can store user data pertaining to one or more social networking engines or platforms. In some implementations, the data stored in the container storage 110 can be encrypted to prevent unauthorized use. The data stored in the container storage 110 can be associated with user-defined privacy levels such that all the information or data stored in the container storage 110 is stored in a zero-knowledge environment and not shared with other users unless explicitly shared by the user 101. Thus, the data stored in the container storage 110 can facilitate encrypted communications between the communication device 140 associated with the user 101 and the server-side virtual machine processes.

In some implementations, the container manager 120 can implement one or more different hash functions to generate hash value(s) or hash string(s) of the received data from the mobile communication device 140 and stored the hash value(s) or hashed string(s) in the container storage 110. The container manager 120 can automate the deployment of applications inside software containers, by providing an additional layer of abstraction and automation of operating system-level virtualization on operating system such as, for example, Linux. In some implementations, an application can include data stored across different containers. In such implementations, the container manager 120 can manage all containers of the application as a single group. In such implementations, the container manager 120 can also cluster the application's containers to optimize resources and provide high-availability.

The container directory 130 can include a list of data associated with the different users that are stored in the container storage 110. The container directory 130 can also partition and list the data associated with different social networking platforms for each individual user. For example, the container directory 130 can delineate the data associated with Facebook for user 101, the data associated with LinkedIn for user 101, the data associated with Snapchat for user 101, and/or the like. The container directory 130 can also store the privacy settings for the data associated with different social networking platforms for each individual user.

Figure 2:
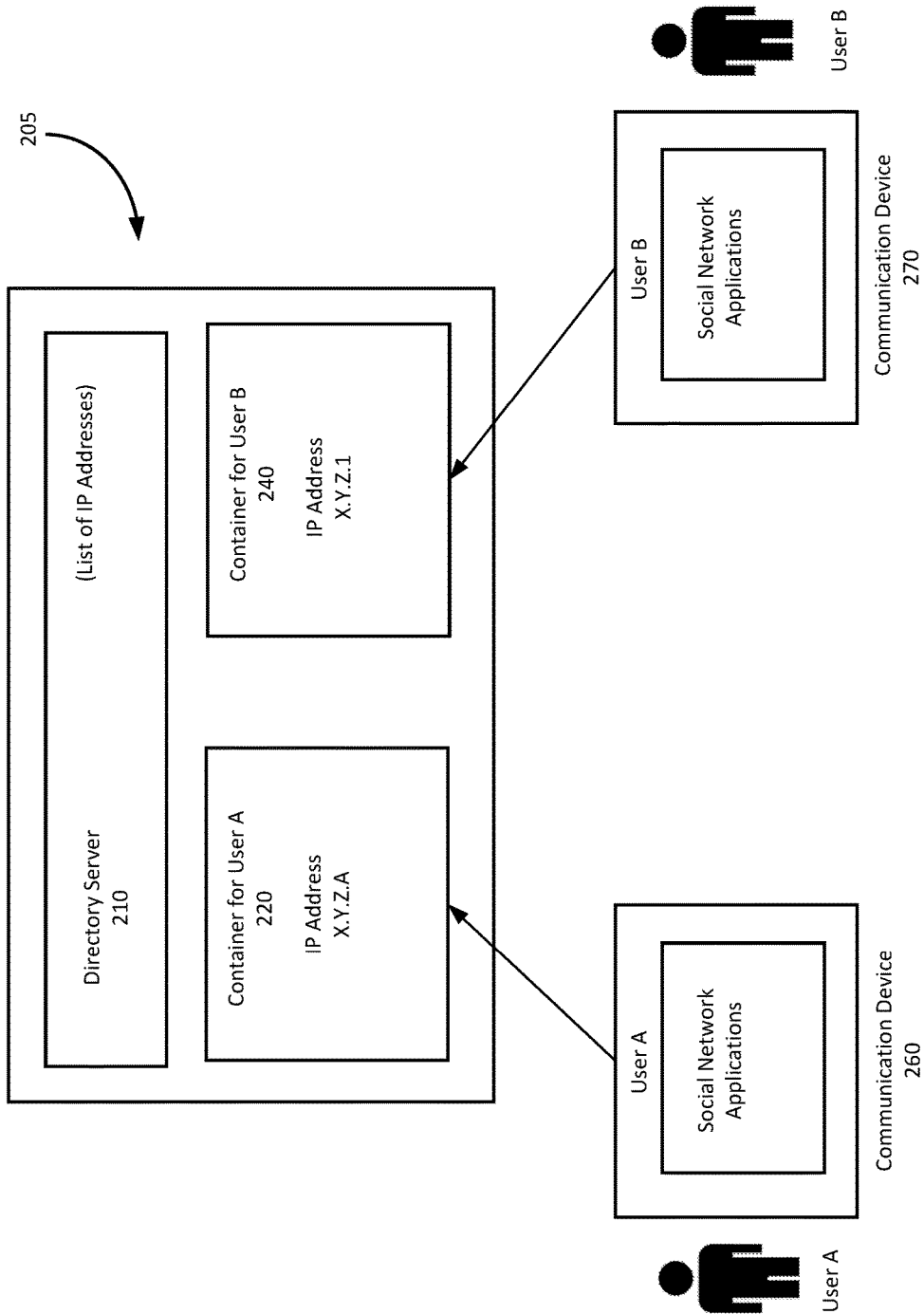
FIG. 2 is a system block diagram of an example system that includes a directory server that manages different containers storing data associated with different users.

FIG. 2 is a system block diagram of an example system 200 that includes a directory server 210 that manages different containers storing data associated with different users. The system 200 includes a directory server 210 that includes a list of internet protocol (IP) addresses that can map to different containers. For example, the directory server 210 includes the IP address (e.g., an IPv6 address) 'X.Y.Z.A' that maps or points to the container 220 that stores data associated with user A, and the IP address (e.g., an IPv6 address) 'X.Y.Z.1' that maps or points to the container 240 that stores data associated with user B. The directory server 210 can also store and/or manage the containers 220 and 240 that store data associated with users A and B, respectively.

As shown in FIG. 2, container 220 has an IP address of 'X.Y.Z.A' and receives data associated with user A from the communication device 260. As described in FIG. 1 (and not shown explicitly in FIG. 2), the communication device 260 can send user data to the container 220 via the Internet (e.g., network 115 as shown in FIG. 1). The data received from the communication device 260 can include data associated with different social networking engines such as, for example, Facebook, LinkedIn, Snapshot, Google+, Xbox1, Twitter, and/or the like. It is to be noted that data associated with user A related to different social networking engines can have different security levels. For example, the Facebook data associated with user A can have a first security level (e.g., security level A) that allows sharing of the data with a first set of pre-determined other users, and the LinkedIn data associated with user A can have a second security level (e.g., security level B) that allows sharing of the data with a second set of pre-determined other users, where security level A can be different from security level B and the first set of users and the second set of users may not overlap. Additionally, user A may elect to include services within the container 220 that operate on its information (or data) to request and display other information, such as advertisements, appropriate for user A without disclosing the information used to target such advertisements to anyone else (e.g., other users). Hence, other users will not have access to the data stored in the container 220 that is associated with user A unless user A explicitly allows sharing of either portions of or the entirety of the data associated with user A with the other users. This environment is known as a zero-knowledge environment where all the data or information stored associated with user A is solely related to user A. User A can also have the capability to control, customize and operate the container 220 from the communication device 260.

As shown in FIG. 2, container 240 has an IP address of 'X.Y.Z.1' and receives data associated with user B from the communication device 270. As described in FIG. 1 (and not shown explicitly in FIG. 2), the communication device 270 can send user data to the container 240 via the Internet (e.g., network 115 as shown in FIG. 1). The data received from the communication device 270 can include data associated with different social networking engines such as, for example, Facebook, LinkedIn, Snapshot, Google+, Xbox1, Twitter, and/or the like. It is to be noted that data associated with user B related to different social networking engines can have different security levels. For example, the Facebook data associated with user B can have a third security level (e.g., security level C) that allows sharing of the data with a third set of pre-determined other users, and the LinkedIn data associated with user B can have a fourth security level (e.g., security level D) that allows sharing of the data with a fourth set of pre-determined other users, where security level C can be different from security level D and the third set of users and the fourth set of users may not overlap. Additionally, user B may elect to include services within the container 240 that operate on its information (or data) to request and display other information, such as advertisements, appropriate for user B without disclosing the information used to target such advertisements to anyone else (e.g., other users). Hence, other users will not have access to the data stored in the container 240 that is associated with user B unless user B explicitly allows sharing of either portions of or the entirety of the data associated with user B with the other users. This environment is a zero-knowledge environment where all the data or information stored associated with user B is solely related to user B. User B can also have the capability from to control and operate the container 240 from the communication device 270.

Figure 3:
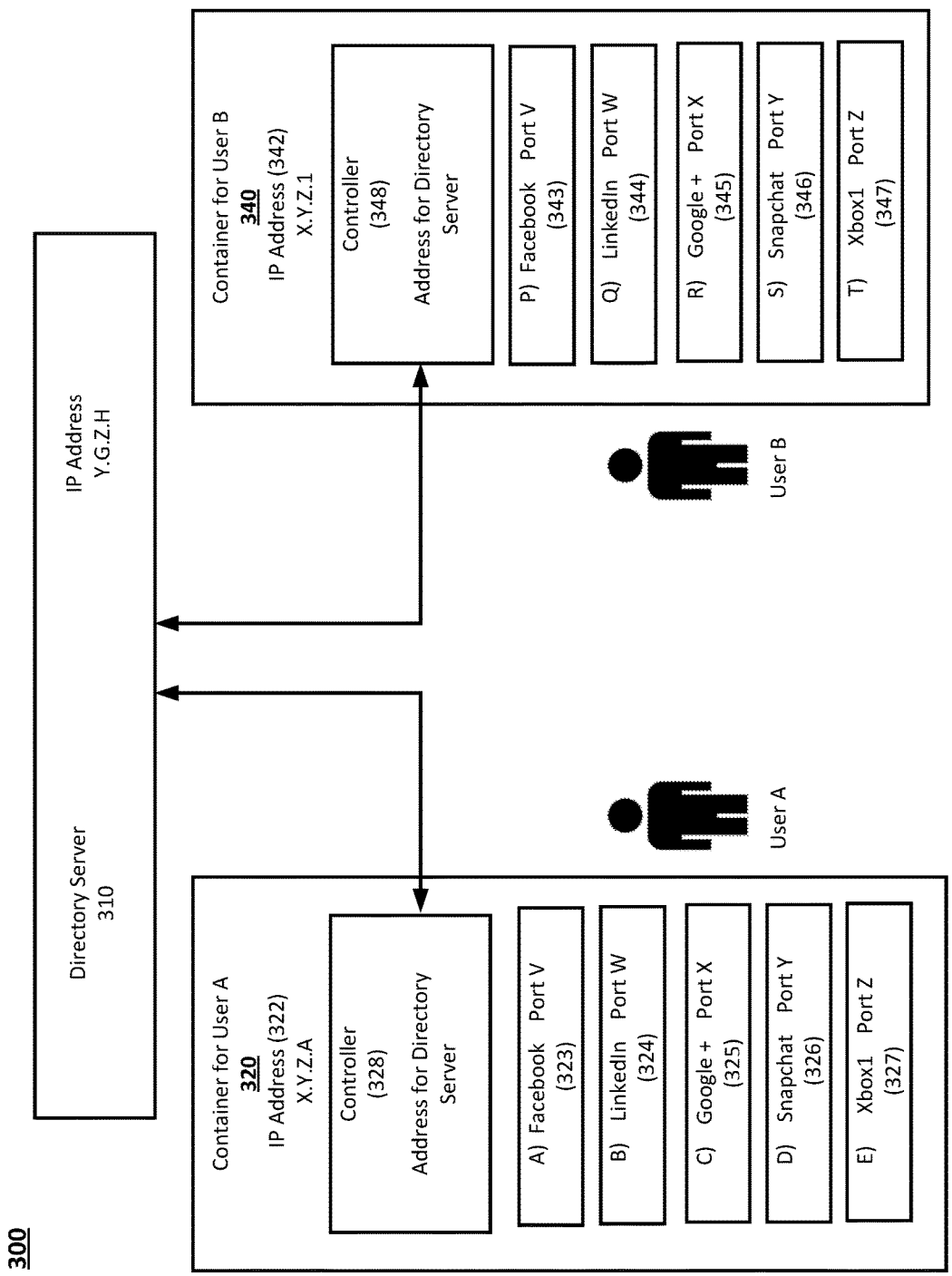
FIG. 3 is a system block diagram of an example system that can provide directory services to data stored in different containers.

FIG. 3 is a system block diagram of an example system 300 that can provide directory services to data stored in different containers. The system 300 includes a directory server 310, a container 320 that stores data associated with user A, and a container 340 that stores data associated with user B. The directory server 310 is similar to the directory server 210 shown in FIG. 2 and can include the IP address (e.g., an IPv6 address) 'X.Y.Z.A' that maps or points to the container 320 that stores data associated with user A and the IP address (e.g., an IPv6 address) 'X.Y.Z.1' that maps or points to the container 340 that stores data associated with user B. The directory server 310 can also store and/or manage the containers 320 and 340 that store data associated with users A and B, respectively.

Container 320 can include data associated with user A that can be partitioned into various subsets. For example, data subset A associated with user A's Facebook account information be received from, for the communication device 260 shown in FIG. 2 via, for example, port V of the device (e.g., a server, a desktop computer, etc.) that implements container 320, data subset B associated with user A's LinkedIn account information can be received via port W of the device that implements container 320, data subset C associated with user A's Google+ account information can be received via port X of the device that implements container 320, data subset D associated with user A's Snapchat account information can be received via port Y of the device that implements container 320, and data subset E associated with user A's Xbox1 account information can be received via port Z of the device that implements container 320.

The controller 328 can be a hardware and/or software module stored in memory and/or executed in a processor of the device that implements container 320. The controller 328 can send and/or receive data units (e.g., data packets) from the mobile communication device associated with user A (e.g., communication device 260 shown in FIG. 2) and can control the type of data and the flow of data being received from the communication device associated with user A. The controller 328 can implement one or more different hash functions to generate hash value(s) or hash string(s) of data associated with user A that is received from the different ports of the device that implements container 320. Examples of different hash generation functions that can be implemented by the controller 328 can include discrete costine transform based hashes, Marr-Hildreth Operator based hashes, radial variance based hashes, discrete wavelet transform based hashes, singular value decomposition based hashes, hashes using feature points, and/or block mean value based hashes.

The controller 328 can automate the deployment of information or data inside container 320 (e.g., by creating different subsets of data related to the different social networking engines described above) by providing an additional layer of abstraction and automation of operating system-level virtualization on an operating system such as, for example, Linux. The controller 328 can also store the IP address of the directory server 320 (e.g., 'Y.G.Z.H') that can manage the functionality of the different containers 320 and/or 340.

Container 340 can include data associated with user B that can be partitioned into various subsets. For example, data subset P associated with user B's Facebook account information can be received from, for the communication device 270 shown in FIG. 2 via, for example, port V of the device (e.g., a server, a desktop computer, etc.) that implements container 340, data subset Q associated with user B's LinkedIn account information can be received via port W of the device that implements container 340, data subset R associated with user B's Google+ account information can be received via port X of the device that implements container 340, data subset S associated with user B's Snapchat account information can be received via port Y of the device that implements container 340, and data subset T associated with user B's Xbox1 account information can be received via port Z of the device that implements container 340.

The controller 348 can be a hardware and/or software module stored in memory and/or executed in a processor of the device that implements container 340. The controller 348 can send and/or receive data units (e.g., data packets) from the mobile communication device associated with user B (e.g., communication device 270 shown in FIG. 2) and can control the type of data and the flow of data being received from the communication device associated with user B. The controller 348 can implement one or more different hash functions to generate hash value(s) or hash string(s) of data associated with user B that is received from the different ports of the device that implements container 340. Examples of different hash generation functions that can be implemented by the controller 348 can include discrete costine transform based hashes, Marr-Hildreth Operator based hashes, radial variance based hashes, discrete wavelet transform based hashes, singular value decomposition based hashes, hashes using feature points, and/or block mean value based hashes. The controller 348 can automate the deployment of information or data inside container 340 (e.g., by creating different subsets of data related to the different social networking engines described above) by providing an additional layer of abstraction and automation of operating system-level virtualization on operating system such as, for example, Linux. The controller 348 can also store the IP address of the directory server 310 (e.g., 'Y.G.Z.H') that can manage the workings of the different containers 320 and/or 340.

In some implementations, interfaces with the containers 320 and 340 may be hierarchically organized so that content undergoes a degree of preliminary processing and organization upon receipt. For example, if the container 320 receives information or data on a first port associated with a first address (e.g., port 'V'), the received data (or content) may be processed as relating to a specified subject matter, whereas if the container 320 receives information or data on a second port associated with a second address (e.g., port 'W'), the received data (or content) may be processed as relating to a different subject matter (e.g., affiliation, "friend status", subject matter or privacy setting).

In some implementations, messages and/or data sent from a first user (e.g., a creator user) to a second user (e.g., a receiver user) can be encrypted by the first user and decrypted by the second user using asymmetric cryptography. Asymmetric cryptography or public-key cryptography is cryptography in which a pair of keys is used to encrypt and decrypt a message so that it arrives to its intended destination securely. Initially, a network user (e.g., the first user) receives a public and private key pair from a certificate authority. Any other user who wants to send an encrypted message can get the intended recipient's (e.g., second user) public key from a public directory. They can use this key to encrypt the message, and they send it to the recipient. When the recipient (e.g., second user) gets the message, they can decrypt it with their private key, which no one else should have access to.

Public-key cryptography, also known as asymmetric cryptography, uses two different but mathematically linked keys, one public and one private. The public key can be shared with everyone, whereas the private key must be kept secret. Rivest-Shamir-Adleman (RSA) is a cryptosystem for public-key encryption, and is widely used for securing sensitive data, particularly when being sent over an insecure network such as the Internet. In RSA cryptography, both the public and the private keys can encrypt a message; the opposite key from the one used to encrypt a message is used to decrypt it. This attribute is one reason why RSA has become the most widely used asymmetric algorithm: It provides a method of assuring the confidentiality, integrity, authenticity and non-reputability of electronic communications and data storage. Many protocols like SSH, OpenPGP, S/MIME, and SSL/TLS rely on RSA for encryption and digital signature functions. It is also used in software programs such as, for example, browsers which need to establish a secure connection over an insecure network like the Internet or validate a digital signature. RSA signature verification is one of the most commonly performed operations in the information technology (IT) sector.

The container may reside on a hosted environment whereby each container is allocated a specified processing commitment. In hosted environments where a controller allocates a processing commitment for a container on a processor (or core on a processor), the processor must first load a container with its one or more applications in the specified state (e.g., saved configuration) from the last period of activation. As the container is activated, the container may await delivery of several messages, such as, for example, those addressed to the IPv6 address for the container. The messages would be encrypted and would need to be decrypted by the container, using, for example, the corresponding symmetric key previously exchanged (or the counterpart asymmetric key). The container loads the applicable key and begins decrypting queued messages.

The contents of the decrypted message may require additional processing. For example, the message may include a request for status information of the container and ask a social networking module within the container to provide an indication of whether a user is available to exchange personal messages. The module then may poll its resources and determine whether the user is in fact available to exchange messages. In launching the query, the container generates an active record requiring a processing follow-up. As the response to the query is received, the active record is updated. When the container cycles through the list of active records requiring subsequent actions, the container generates a responsive message, encrypts the message with the key for the remote recipient, and sends the message to the remote sending container.

In one configuration, where multiple applications and frameworks are being hosted inside a container, the IPv6 packet may be coded with labels and parameters to indicate the constituent application. For example, some applications may only receive a miniscule processing commitment and may be queued for longer cycles, whereas other applications may justify more frequent processing and require the container to process the message within the next cycle.

Figure 4A:
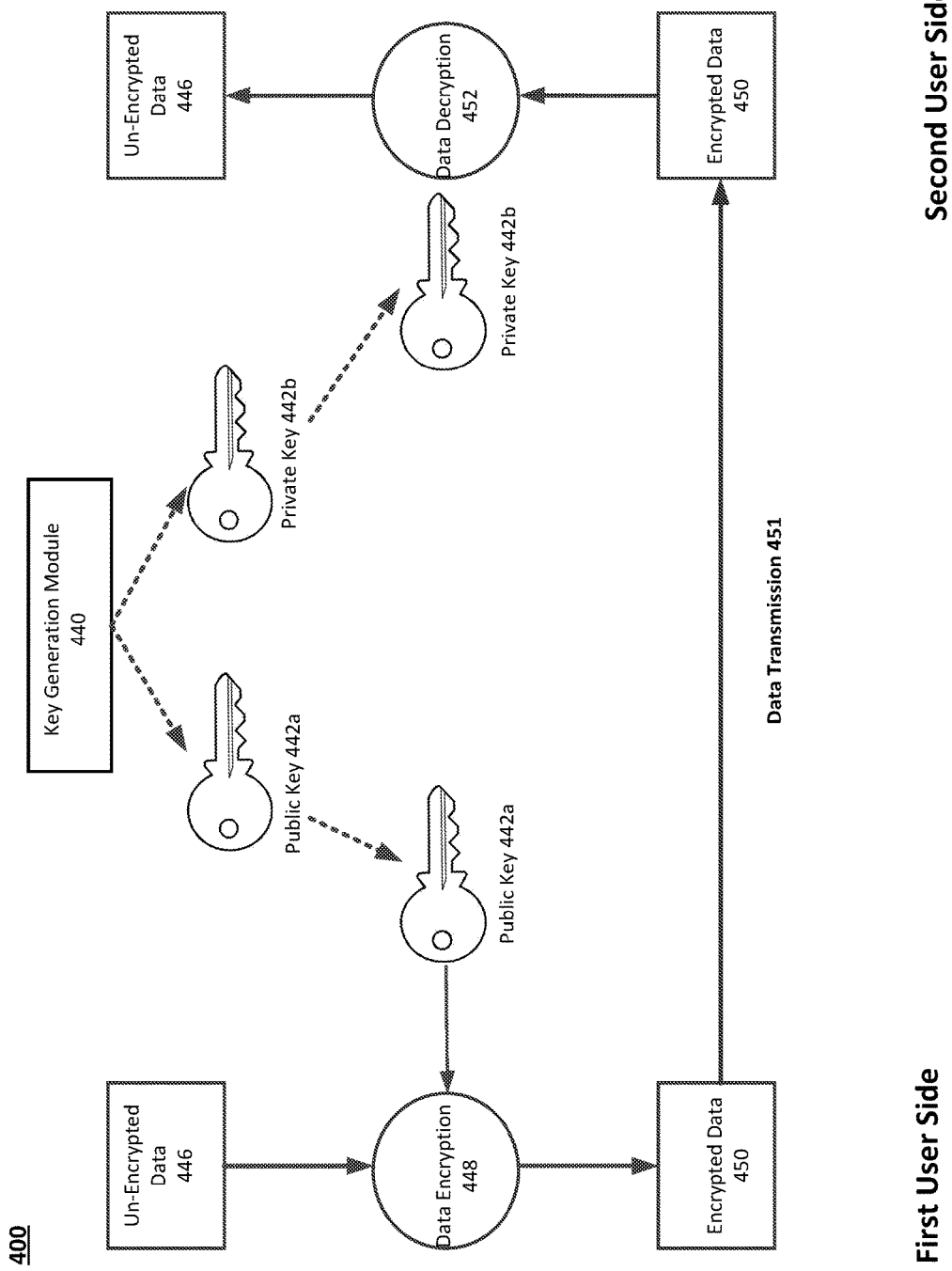
FIG. 4A illustrates an example method for data encryption and decryption using asymmetric cryptography for secure transmission of data between a first user and a second user, respectively.

FIG. 4A illustrates an example method for data encryption and decryption using asymmetric cryptography for secure transmission of data between a first user and a second user, respectively. The RSA method for public-key encryption 400 involves a user device associated with the second user (i.e., the receiver user) that includes a certified key generation module 440 that can use an asymmetrical algorithm (e.g., RSA) to create a public key 442a and private key 442b pair and transmit and store the public key 442a and private key 442b in the container associated with the second user (e.g., container 320 or 340 as shown in FIG. 3). The second user can choose to provide the public key 442a to any other users with which the second user wishes to share information (e.g., friends in a Facebook friend's list, LinkedIn users list, etc.). The first user (e.g., a creator user) can use the public key 442a to encrypt un-encrypted data 446 (e.g., an email, a text message, a photograph, a MS WORD document, or any other suitable data) at the data encryption stage 448. The data can be, for example, image files (e.g., JPEG files, TIFF files, GIF files, etc.), word processor files (e.g., Microsoft® Word files, etc.), portable document files (e.g., PDF files), spreadsheets, and/or the like. The encryption process leads to the creation of the encrypted data 450 which can be stored in the container associated with the first user (i.e., one copy stored for backup) and transmitted to the second user at the data transmission stage 451.

The received encrypted data 450 can be stored at any suitable located within the container associated with the second user and addressed with unique identifiers, such as an IPv6 address. The application (i.e., Facebook, LinkedIn, Twitter, Microsoft Outlook, Microsoft Word, etc.) running on the container associated with the second user can retrieve the private key 442b and decrypt the encrypted data at the data decryption stage 452 to generate the un-encrypted data 446. The un-encrypted data 446 can then be displayed on the display unit of the user device associated with the second user (visual data) and/or output through a microphone connected to the user device associated with the second user (e.g., audio data).

Figure 4B:
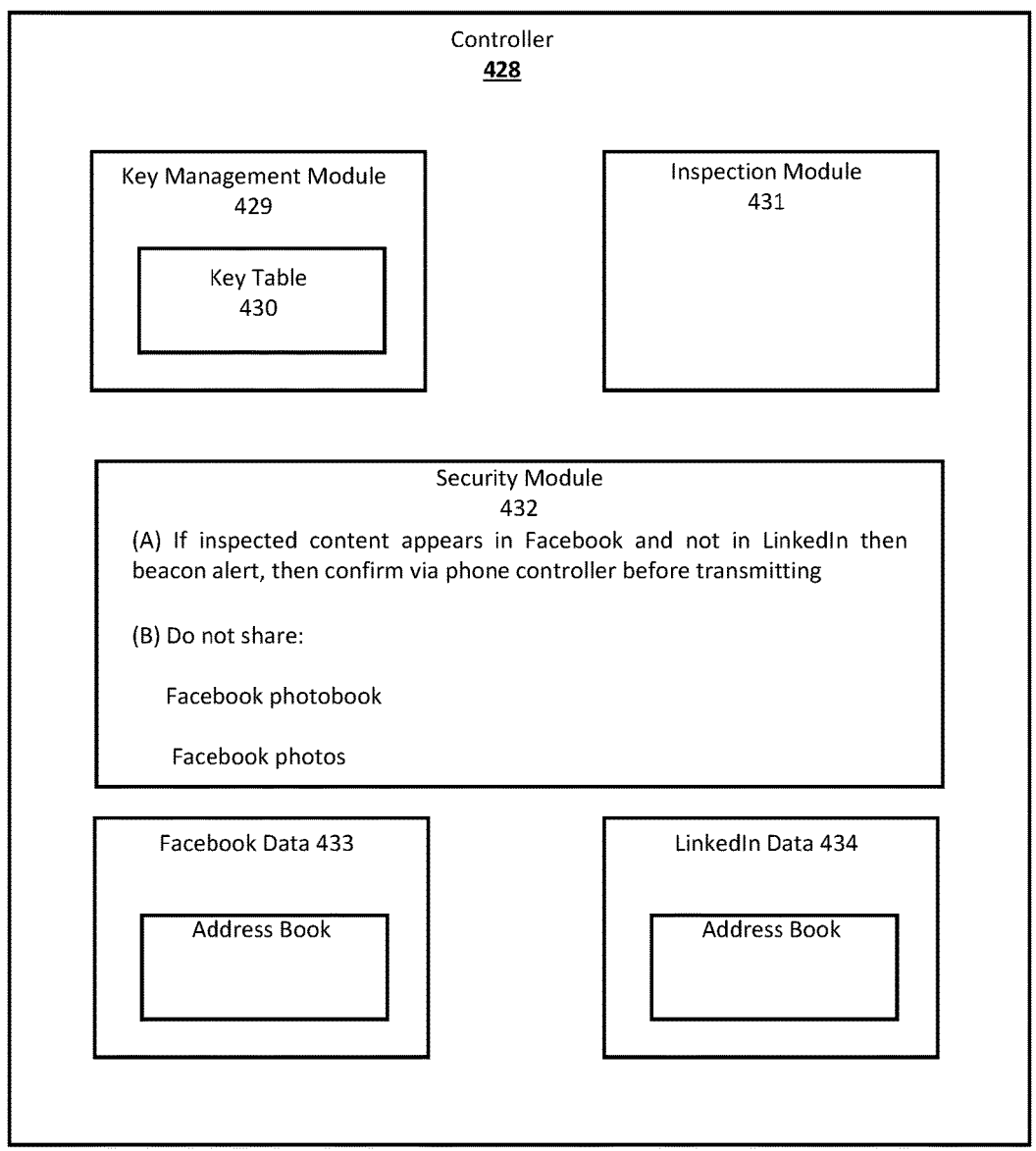
FIG. 4B is a screenshot of an instance of a graphical user interface (GUI) for interacting with a controller that can control the type of data and the flow of data being received at a container from a communication device associated with a user.

FIG. 4B is a screenshot of an instance of a graphical user interface (GUI) 400 for interacting with a controller 428 that can control the type of data and the flow of data being received at a container from a communication device associated with a user. The controller 428 is similar to the controller 328 shown in FIG. 3. The GUI 400 can be displayed on a display unit of the device (e.g., a server, a desktop computer, etc.) that implements a container. The display unit can be, for example, a liquid crystal display (LCD) unit or a light emitting diode (LED) alpha-numeric display unit that can display the graphical user interface (GUI) 400. The GUI 400 can allow a user to interact with the container storing the user's data. The GUI 400 may include a set of displays having message areas, interactive fields, pop-up windows, pull-down lists, notification areas, and buttons that can be operated by the administrator. The GUI 400 may include multiple levels of abstraction including groupings and boundaries. It should be noted that the term "GUI" may be used in the singular or in the plural to describe one or more GUI's, and each of the displays of a particular GUI may provide the user of the container with a user-friendly interactive environment and information associated with the user data. The GUI 400 of the controller 428 includes a display of a key management module 429, an inspection module 431, and a security module 432 that can access data associated with different social network engines related to the user.

The key management module 429 can be a hardware and/or software module stored in memory and/or executed in a processor of the device that implements a container. The key management module 429 can implement one or more different hash functions to generate hash value(s) or hash string(s) of data associated with a user that is received from the different ports of the device that implements a container (e.g., container 320 shown in FIG. 3). Examples of different hash generation functions that can be implemented by the key management module 429 can include discrete costine transform based hashes, Marr-Hildreth Operator based hashes, radial variance based hashes, discrete wavelet transform based hashes, singular value decomposition based hashes, hashes using feature points, and/or block mean value based hashes. In some implementations, the hash value or string generated of the data associated with a user (e.g., data associated with user A as shown in FIG. 3) can have a high degree of exclusivity such that any (accidental or intentional) change to the data associated with the user may (with very high probability) change the hash value of the data. Additionally, the hash value for the data associated with user can be generated in such a manner that it may not be feasible to re-generate the data back from its given hash value, and it may not be feasible to find two different set of data with the same hash value. After performing the hash operations, the key management module 429 can store the hash values or hash strings of the hashed data in a key table 430 (e.g., a hash table).

In some implementations, the key management module 429 can store the different public-private key pairs for different users associated with different containers. For instance, the key implementation module 429 can store the public-private key pairs for a user that is generated by the user device associated with the user and transmitted to the key management module 429 from the key generation module 440 of a user device.

The inspection module 431 can be a hardware and/or software module stored in memory and/or executed in a processor of the device that implements a container. The inspection module 431 can use any suitable number of techniques to inspect and/or analyze the data associated with different social networking engines that are related to different users. The inspection module 431 can output the results of the inspection or the analysis operations to the security module 432.

The security module 432 can be a hardware and/or software module stored in memory and/or executed in a processor of the device that implements a container. The security module 432 can receive data from the inspection module 431 that includes the results of rigorous analysis steps (or operations) performed by the inspection module 431 and can perform further analysis on the received data. In one example, as shown in FIG. 4B, the user can configure the security module 432 to determine if a set of data (i.e., content) received by the container appears on (i.e., associated with) a user's Facebook account and not the user's LinkedIn account. If so, the user can configure the security module 432 to activate an alarm mechanism and validate the received data with a controller of the communication device sending the data before transmitting the data for storage in the container. In another example, as shown in FIG. 4B, the user can configure the security module 432 to set the security settings of the received Facebook data associated with the user, whereby any photos or entire photobooks or albums from the user's Facebook profile are not shared with any other users associated with the container or any other container operably coupled to containers 320 or 340 (as shown in FIG. 3). The security module 432 can have access to a user's social networking data such as a user's Facebook data 433 and/or a user's LinkedIn data 434 to perform the analysis operations.

FIG. 5 is a screenshot of an instance of a graphical user interface (GUI) 500 of a container manager 521 that can manage different containers. The GUI 500 can be displayed on a display unit of the device (e.g., a server, a desktop computer, etc.) that implements a container. The GUI 500 of the container manager 521 shows a list of container identifiers (Container ID) of containers that are managed by the container manager 521 such as, for example, container ID '00', '01' and '02'. The GUI 500 of the container manager 521 also shows the IP address of the different containers managed by the container manager 521 such as, for example, container '00' has an IP address of 0.123, container '01' has an IP address of 0.124, and container '02' has an IP address of 0.125. The GUI 500 of the container manager 521 also shows the service level of the different containers managed by the container manager 521 (e.g., service level A, B or C). The GUI 500 of the container manager 521 displays the number of supplemental applications running on the different containers managed by the container manager 521. For example, container '00' is running two supplemental applications, container '01' is running three supplemental applications, and container '02' is running ten supplemental applications.

The GUI 500 of the container manager 521 displays the parameters of the different service levels provided by the containers managed by the container manager 521. For example, service level 'A' (or service category 'A') can be associated with 100 processing unit cycles (PUC), a 2 GB main memory space, a bandwidth of 10X and a second tier storage of 1 TB. Service level 'B' (or service category 'B') can be associated with 10 processing unit cycles (PUC), a 20 MB main memory space, a bandwidth of 2× and a second tier storage of 2 GB. Service level 'C' (or service category 'C') can be associated with 1 processing unit cycle (PUC), a 10 MB main memory space, a bandwidth of 0.01X and a second tier storage of 1 GB.

Figure 6:
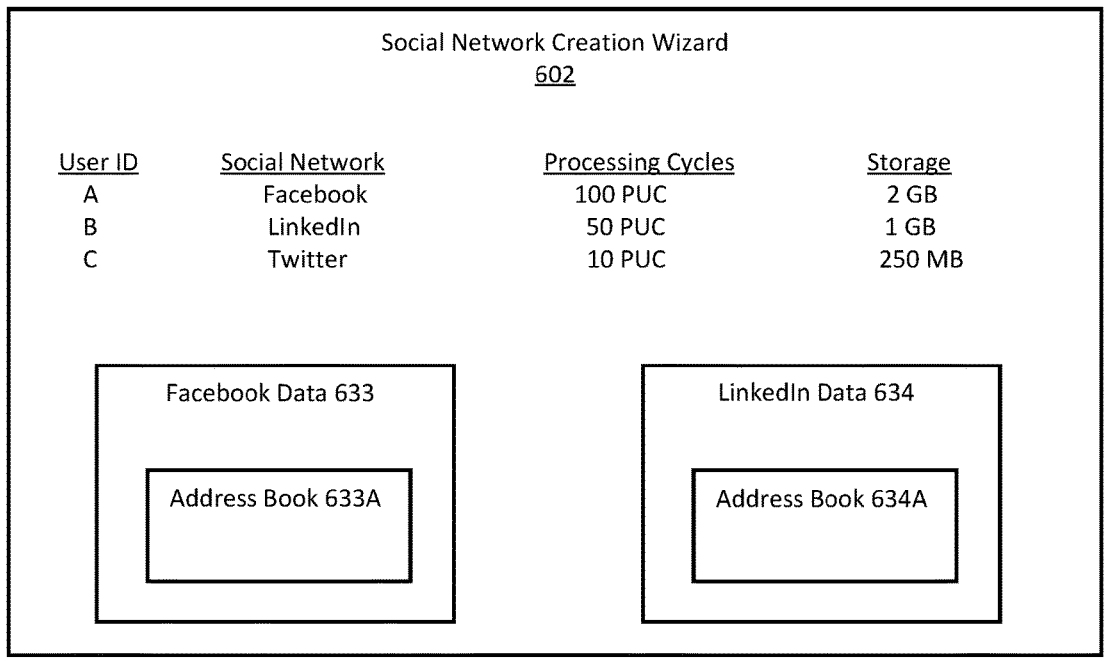
FIG. 6 is a screenshot of an instance of a graphical user interface (GUI) for a social network creation wizard.

FIG. 6 is a screenshot of an instance of a graphical user interface (GUI) 600 for a social network creation wizard 602. The GUI 600 can be displayed on a display unit of the device (e.g., a server, a desktop computer, etc.) that implements a container. The social network creation wizard 602 can include data associated with different social networking engines (e.g., Facebook data 633, LinkedIn data 634) associated with different users. The address book 633A and 634A locates the address of the data associated with each user for a particular social networking engine, respectively (i.e., Facebook and LinkedIn).

The GUI 600 of the social network creation wizard 602 can include data associated with creating (and maintaining) different social network profiles for different users. For example, as seen in FIG. 6, the GUI 600 shows a Facebook profile created for user A involves 100 processing unit cycles (PUC) and 2 GB of memory, a LinkedIn profile created for user B involves 50 PUC and 1 GB of memory, and a Twitter profile created for user C involves 10 PUC and 250 MB of memory.

FIG. 7 is a screenshot of an instance of a graphical user interface (GUI) 700 for a social network administration tool 703. The GUI 700 can be displayed on a display unit of the device (e.g., a server, a desktop computer, etc.) that implements a container. The social network administration tool 703 can include administration data for maintaining social network profiles of different users in different containers. For example, the GUI 700 shows the Facebook user profile associated with user A is being contained at container '00' that is currently being implemented at a primary device with a device ID of 'AA'. As described above, the containers may be migrated or moved from a primary device to a backup device depending on device or virtual machine load, social network computational burden (e.g., number of interconnections), changing security requirements (e.g., receiving a security alert or indication of compromise or suspicious activity), or logical requirement (e.g., a desire to configure or develop another instantiation of a new social network or social subnetwork (interest community)). For the case of container '00', container '00' can be migrated from the primary device 'AA' to the backup device 'BB' if any of the adverse conditions described above occurs. The container '00', however, is currently being implemented in device AA because a bandwidth of 500 MB is still available to device 'AA'. The GUI 700 also shows that the LinkedIn user profile associated with user B is being contained at container '01' that is currently being implemented at a primary device with a device ID of 'BB' as a bandwidth of 200 MB is still available to device 'BB'. FIG. 7 further shows that the Twitter user profile associated with user C is being contained at container '02' that is currently being migrated from device 'CC' to device CAA as no further bandwidth is available to device 'CC'.

FIG. 8 is a screenshot of an instance of a graphical user interface (GUI) 800 for a container administration tool 804. The GUI 800 can be displayed on a display unit of the device (e.g., a server, a desktop computer, etc.) that implements a container. The container administration tool 804 can include administration data for maintaining different containers in different devices.

Typically, (social networking) containers may be configured to maintain both public and private interfaces. For example, a virtual machine may maintain an address book of addressing information (or manage another virtual machine that manages addresses and contact information) so that a user can contact other users using existing messaging mechanisms (e.g., private messages, email, text messaging, etc.). The container also may maintain an anonymous messaging address that actively screens all content for personally-identifiable information. In this sense, the public and private virtual interfaces, respectively, may assist a user with maintaining (1) a "real world" interface where other users may contact the user in an identifiable way, (2) a "virtual" interface configured to support anonymous or virtual identity communications.

The container may be configured to port social networking constructs from existing social network engines into newly-formed social networks. For example, a user may interface with a migration system that allows the user to load an existing social network (e.g., Facebook or Twitter) into a new social network. The migrated social network quantum of data may allow the user to preserve a greater degree of privacy and/or security restrictions, preserve legacy data, and/or leverage existing relationships as a micro-social network is being established.

In FIG. 8, the GUI 800 of the container administrator tool 804 shows that container '00' can be associated with a device with an IP address '0.123' and stores information or data associated with supporting a Facebook profile (or user account) of user A, has a public interface so that user A can contact other users using existing messaging mechanisms, has a primary device ID of 'AA', and a backup device ID of 'BB'. In FIG. 8, the GUI 800 of the container administrator tool 804 also shows that container '01' can be associated with a device with an IP address '0.124' and stores information or data associated with supporting a LinkedIn profile (or user account) of user B, has a public interface so that user B can contact other users using existing messaging mechanisms, has a primary device ID of 'BB', and a backup device ID of 'CC'. In FIG. 8, the GUI 800 of the container administrator tool 804 further shows that container '02' can be associated with a device with an IP address '0.126' and stores information or data associated with supporting a Man UTD Fan profile (or user account) of user C, has a private interface so that user C can support anonymous or virtual identity communications, has a primary device ID of 'CC', and a backup device ID of 'AA'. In this case, a fan (i.e. user C) of the English football club Manchester United may not want to share the personal identification information with other users or fans as user C can publish commentary on the performance of their team and prefers publishing such commentaries anonymously. Hence, user C or the fan uses a private interface to communicate with other users or fans.

FIG. 9 is a screenshot of an instance of a graphical user interface (GUI) 900 for a social network associated with a Manchester United Fan Forum 902. The GUI 900 can be displayed on a display unit of the device (e.g., a server, a desktop computer, etc.) that implements a container. The GUI 900 shows a list of members in the Manchester United Fan Forum 902 (Legion_of_Rooney, Alex_Ferguson), the IP addresses of the container storing data of the user profiles (e.g., 'X.Y.Z.A', 'X.Y.Z.B'). In FIG. 9, the GUI 900 of the Manchester United Fan Forum 902 shows that security configurations of the Manchester United Fan Forum 902 can be published, can maintain active sockets, with a period of pulling of two minutes and can allow messaging applications but does not allow any undefined constituent applications.

Figure 10:
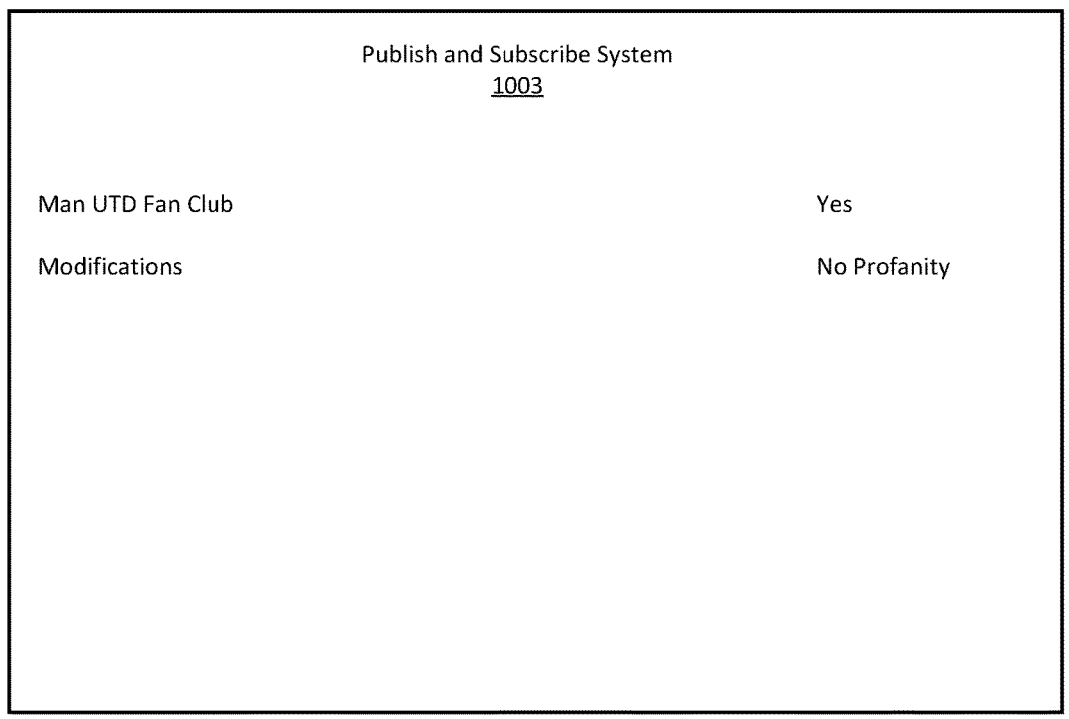
FIG. 10 is a screenshot of an instance of a graphical user interface (GUI) for managing the containers associated with the Manchester United Fan Forum social network that can be configured to interface with a publish-and-subscribe content distribution system.

FIG. 10 is a screenshot of an instance of a graphical user interface (GUI) 1000 for managing the containers associated with the Manchester United Fan Forum social network that can be configured to interface with a publish-and-subscribe content distribution system 1003. For example, in some instances, a fan of certain English football clubs (e.g., Manchester United) may not want to share the identification information as the fan publishes commentary on the performance of their team. Thus, the publish-and-subscribe system 1003 may be configured to publish the fan's commentary using certain labels (e.g., hash tags or semantic identifiers) for consideration by other fans. Similarly, a publish-and-subscribe system 1003 may be configured to receive from other network members (i.e., fans) where the content relates to the specified labels or where the user has an established relationship. The container may be configured to develop a broad or granular profile so that users in need of more information may receive information related to, for example, all English Premier League teams while fans only interested in a specified club (e.g., Manchester United) would only receive information related to their preferred club and not receive information related to competing clubs (e.g., Chelsea). The publish-and-subscribe system 1003 may be configured to develop a broader dictionary than terms specifically provided by or identified by a user. Where the user repeatedly focuses on certain topics, the system 1003 may be configured to identify topical labels and constituent terms within that topical label. In FIG. 10, the publish-and-subscribe content distribution system 1003 can allow the users or fans of the Manchester United Fan Forum social network to publish commentary on the performance of their team and thus publish the fan's commentary using certain labels (e.g., hash tags or semantic identifiers) for consideration by other fans. FIG. 10 also shows that the publish-and-subscribe content distribution system 1003 does not allow the users or fans of the Manchester United Fan Forum social network to publish any profanities.

Figure 11:
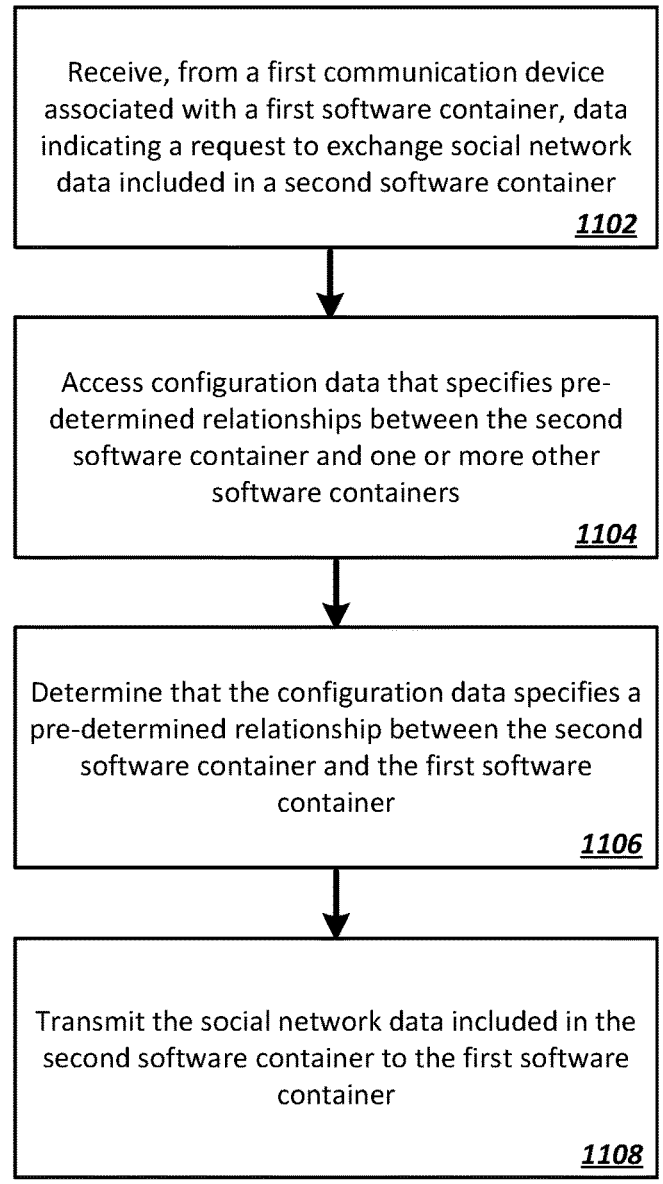
FIG. 11 is a process performed by a system that can provide a zero-knowledge environment for social networking based on containers.

FIG. 11 is a flowchart depicting a process 1100 performed by a system that can provide a zero-knowledge environment for social networking based on containers. For example, the process 1100 can be performed by the system 300 of FIG. 3, or another system that is capable of providing a zero-knowledge environment for social networking using a software container architecture.

The system can receive, from a first communication device associated with a first software container related to a first online user identity, data indicating a request to exchange social network data included in a second software container related to a second online user identity (1102). As described, each of the first software container and the second software container can be an independent server virtualization instance that is configured to operate independently of other processes operating on a same processing resource as the independent server virtualization instance. The request to exchange social network data can comprise at least a first network address that uniquely identifies the first software container and a second network address uniquely identifying the second software container.

For example, the system 300 can receive data indicating a request to exchange social network data from a communication device that is associated with the software container 320 related to the user A. The request can be one to receive social network data included in the software container 340 related to the user B. In some implementations, the data indicating the request can be received by an application instance operating on a communication device associated with the user A, such as an application associated with the system 300, e.g., a social network application for a zero-knowledge social network. Alternatively, the data indicating the request can be received by the controller 328 of the container 320. The data indicating the request can also include information identifying the first and second software containers, where such information may be first and second network addresses that each uniquely identify a single software container. Such network addresses may be, for example, IPv6 or DNS addresses. In some instances, the first and second software containers can exist on users' communication devices. For example, the first software container may be hosted on the first communication device, and the second software container may be hosted on a second communication device. The communication devices may be those of the users to whom the online user identities correspond. For example, user A may have a first online user identity, and the container 320 associated with the first online user identity may belong to the user A. Similarly, user B may have a second user identity, and the container 340 associated with the second online user identity may belong to the user B. Alternatively, the containers 320, 340 may be hosted remotely from the communication devices, e.g., at a cloud service, and in such cases the data indicating the request may be received by the system, e.g., a social network system, from a communication device over one or more networks, and/or may be received by the controller 328 of the container 320 that is hosted in the cloud over one or more networks.

The system can access configuration data that specifies pre-determined relationships between the second software container and one or more other software containers (1104). Each of the pre-determined relationships specified by the configuration data can permit social network data to be exchanged between the second software container and the one or more other software containers. Additionally, each of the pre-determined relationships between the second software container and the one or more other software containers can be specified by a second communication device that is associated with the second software container.

For example, the container 340 relating to the user B can store configuration data locally in the container 340, or configuration data relating to the container 340 can be stored externally to the container 340 in the system 300, for example, such that the configuration data is accessible at the directory server 310 or at another server associated with the system 300. The configuration data may include pre-determined relationships, that is, relationships between the second container 340 and other containers, where a relationship enables information to be exchanged between the containers. In some implementations, the only device that may be able to modify the configuration data associated with the second container 340 may be the communication device that is associated with the container 340, thereby giving the user B exclusive control over the relationships between their container 340 and other containers. Such control allows the user B to completely control how information in their container 340 is shared with other users and entities of the zero-knowledge social network.

In some implementations, the configuration data may include additional information in relation to the pre-determined relationships, such as security levels associated with the pre-determined relationship that govern which social network data may be provided to other containers, thereby giving the user further control over how information in their container is shared within the social network. In some implementations, a pre-determined relationship between two containers may be a publish-and-subscribe relationship, such that a container may be indicated as only publishing information to one or more other containers, only subscribing to information that has been published in one or more other containers, or both publishing and subscribing to information that is in other containers. This provides additional control to a user, in that they may control who sees which information in their container, as well as what information they receive, e.g., from other containers, from advertising entities, and so on.

The system determines that the configuration data specifies a pre-determined relationship between the second software container and the first software container that permits social network data to be exchanged between the second software container and the first software container (1106). For example, the system can inspect the accessed configuration data and determine that a pre-determined relationship between the first and second software containers is specified by the configuration data. The system may further determine that the pre-determined relationship between the first and second software containers permits the social network data included in the second software container to be exchanged with the first software container, that is, such that the social network data in the second software container may be provided to the second software container such that the social network data in the second software container can be presented for output at the first communication device associated with the first software container.

For instance, the controller 348, an application associated with the system 300, or another component of the system 300 may inspect the configuration data associated with the second container 340 that is stored at the second container 340 or elsewhere in the system 300, and may determine that the configuration data specifies a pre-determined relationship between the two software containers 320, 340. The configuration data may further specify that the pre-determined relationship between the two software containers 320, 340 enables the social network data, e.g., the data subset P associated with user B's Facebook social network data 343, to be exchanged with the first software container 320.

Determining that the social network data can be exchanged with the first software container 320 may include determining that the social network data is identified as having been published. For example, the user B can indicate when to publish social network data that is included in their container 340, such that the social network information is only provided to the container 320 if it has been published by the user B. Such a feature ensures that only the social network data that user B wants to share in the social network will be shared, and that other users or entities associated with the social network cannot access this social network data until it has been published. In some implementations, a default setting for the publish-and-subscribe system may be that social network data is automatically published, such that subscribers can access the social network data once it has been added by the user B and stored in the second container 340.

Based on determining that the configuration data specifies a pre-determined relationship between the second software container and the first software container that permits social network data to be exchanged between the second software container and the first software container, the social network data included in the second software container is transmitted to the first software container (1108). For example, based on determining that the configuration data associated with the second software container includes a pre-determined relationship between the second software container and the first software container, and determining that the pre-determined relationship permits the social network data to be transmitted to the first software container, the social network data, e.g., a copy or a pointer to the data, can be transmitted to the first software container. Based on receiving the transmission including the social network data included in the second software container, the first communication device associated with the first software container may provide the received social network data for output at the first communication device.

For example, based on determining that the data set P associated with user B's Facebook social network data 343 that is stored in the container 340 can be exchanged with the container 320, a copy or pointer to the data set P can be transmitted to the container 320. In some implementations, the decision to transmit the social network data to the container 320 can be made by the controller 348 of the container 340, and the transmission of the social network data can be received by the controller 328 of the container 320. In response to receiving the transmission, the system 300, e.g., the controller 328 or an application instance operating on the first communication device associated with the container 320, can also present the received social network data for output at the first communication device. For example, based on receiving social network data corresponding to a social network profile of the second online user identity related to the second container 340, the first communication device associated with the container 320 can provide the social network profile of the second online user identity for output at a display of the first communication device. In some implementations, the system 300 may store the received social network data at the first software container 320. In other implementations, the social network data transmitted from the second software container 340 may be received through the system 300 by an application instance operating on the first communication device, such that the first communication device can present the social network data included in the second container 340 without needing to access the social network data at the first software container 320. In some implementations, the social network data may be provided to the application instance on the first client device for output without the social network data being provided to the first software container. This effectively would allow a user, such as user A, of the first communication device associated with the first software container 320, to view the social network data included in the second software container 340 without such information being transmitted to another software container.

Similar processes may also be used by a communication device to obtain permission to add social network information to a container. For example, a user of the second communication device and having the second online user identity may wish to add information to a social network profile that is stored in the second software container that is related to the second online user identity. To permit the user to add the information to the social network profile, the system can perform a process. Such a process may include receiving, from the second communication device, data indicating a request for the second network address that uniquely identifies the second software container, wherein the request includes social network authorization information corresponding to the second online user identity. The system can then authorize the second communication device to add social network data relating to the second online user identity to the second software container based at least on the social network authorization information corresponding to the second online user identity. Based on authorizing the second communication device to add social network data relating to the second online user identity to the second software container, the system transmits, to the second communication device, information indicating the second network address uniquely identifying the second software container. The system then receives from the second communication device, social network data and information specifying the second network address uniquely identifying the second software container. The social network data received from the second communication device is then stored in the second software container, as the social network data included in the second software container discussed in conjunction with the process 1100, based at least on authorizing the second communication device to add social network data relating to the second online user identity to the second software container and receiving the information specifying the second network address uniquely identifying the second software container. Relying on the system of FIG. 3, for example, the user B may be using a communication device that is in communication with the system 300, and may submit a request to add Facebook social network data to the container 340 that is related to user B's Facebook social network account. User B can include, with their request, social network authorization information, such as a username and password, that can be received by the system 300, e.g., at the directory server 310, the controller 348 of the container 340, or another component of the system 300. The username and password submitted by user B can be verified such that the communication device being used by user B is authorized, e.g., to add social network data to user B's Facebook social network account. To enable the authorized communication device to add information to the software container 340, the system 300 can provide the communication device with the network address that uniquely identifies the second software container 340, e.g., the appropriate IPv6 or DNS address. The system 300 can subsequently receive social network data from the authorized communication device, wherein the social network data can be associated with information specifying the network address that uniquely identifies the second software container 340. The received social network data can be stored at the second software container 340 based on the received social network data being received along with information that specifies the network address that uniquely identifies the second software container 340.

In some implementations, the system may utilize a publish-and-subscribe system to exchange information between software containers. In such a case, the process 1100 of FIG. 11 may include additional steps for determining whether the social network data can be transmitted to the first software container. For example, the process may include determining, based on the configuration data, that the social network data included in the second software container is included among published social network data included in the second software container, wherein including social network data among published social network data enables corresponding subscribers to the published social network data to access the published social network data. The process may further include determining, based on accessing second configuration data that specifies pre-determined relationships between the first software container and one or more other software containers, wherein each pre-determined relationship between the first software container and one or more other software containers is specified by the first communication device and permits social network data to be exchanged between the first software container and the one or more other software containers, that the first online user identity is a subscriber to the published social network data included in the second software container. Finally, the system can transmit the social network data included in the second software container to the first software container based on determining that the social network data included in the second software container is included among published social network data included in the second software container, and determining that the first online user identity is a subscriber to the published social network data included in the second software container.

Additionally, in some implementations, each of the first software container and the second software container is associated with controls that permit access to data stored at the software container according to privacy rules. Such controls may enable a social network or other service maintaining such software containers to comply with domestic, local, or international privacy regulations.

Additionally, in some implementations, the second software container includes social network data relating to two or more different social networks. Thus, as shown in FIG. 3, each of the containers 320, 340 can include social network information for multiple social networks that all relate to the same individual user, e.g., a Facebook, LinkedIn, Google+, and other social network accounts that all relate to the same user B.

As discussed, in implementations of the zero-knowledge system discussed, the data indicating the request to exchange the social network data is received from a social network application instance operating on the first communication device, wherein the social network application instance is associated with the social network engine. Such social network applications, as shown hosted on the devices 260, 270 of FIG. 2, enable fairly small applications to operate on individual users' communication devices that enable the users to interact with the containers of the zero-knowledge social network; e.g., to view information being exchanged in the social network. Such an application may permit, as an addition to the process 1100, providing the social network data included in the second software container for output at a display of the first communication device.

As discussed previously with respect to the network addresses that uniquely identify the software containers of the process 1100, the first network address uniquely identifying the first software container may be a first IPv6 or DNS address that points to the first software container and that does not point to any additional software containers, and the second network address uniquely identifying the second software container may be a second IPv6 or DNS address that points to the second software container and that does not point to any additional software containers.

Additionally, to provide added security in the exchange of information between containers in the system, transmitting the social network data included in the second software container to the first software container may comprise encrypting the social network data before transmission and decrypting the encrypted social network data upon receipt. For example, the transmission process may include encrypting the social network data using a public encryption key that is included in the second software container, transmitting the encrypted social network data to the first software container, and decrypting the encrypted social network data using a private encryption key that is included in the first software container.

Moreover, to provide for added control of the user over the information included in their container and how that information is shared, the configuration data discussed with respect to the process 1100 may be included in the second software container.

The containers described in FIGS. 1-11 can be configured to act in a zero-knowledge environment so that all information stored in the containers associated with social network engines related to a user is solely that of the user unless explicitly shared by the user. The containers may be configured to participate in a publish-and-subscribe network in order to share information. In addition, the containers may be provisioned with controls so that global operators may comply with local privacy rules. In some implementations, the containers or virtual machines may be configured with unique identifiers, such as IPv6 or a DNS address, which is directly Internet addressable. The containers may be assigned to individuals and may be configured to be easily provisioned and moved between devices.

In some implementations, a container may be configured to include advertising. However, the advertising service may be configured to operate without any information for a prospective candidate thus conforming to act in a zero-knowledge environment. In such implementations, the use of modular containers may be used to reduce and/or eliminate the need for complex application framework that publishes content between users. This, in turn, may facilitate scaling to large audiences. The containers may be configured to interoperate between multiple services. Hence, the same container may be configured to operate both in micropublishing environments (e.g., Twitter) and in more computationally complex environments (e.g., Facebook).

In another configuration, the container may be used to generate its own profile and/or tag and share that tag with an advertising server, which can then provide an advertisement responsive to the shared tag. In still another configuration, an advertising engine within the container periodically downloads a collection of information describing various advertisements and identifies an advertisement identified by the advertising engine. Alternatively, the advertising engine may inspect suggested advertisements from an advertising server and find an advertisement responsive to the perceived interests of the user. If a tag is shared, the tag may specify interests or key words responsive to the user's interests. Still, other tags may include some descriptive personal information that is supported by the user's specified permission level and/or has been authorized for release by the user.

Figure 12:
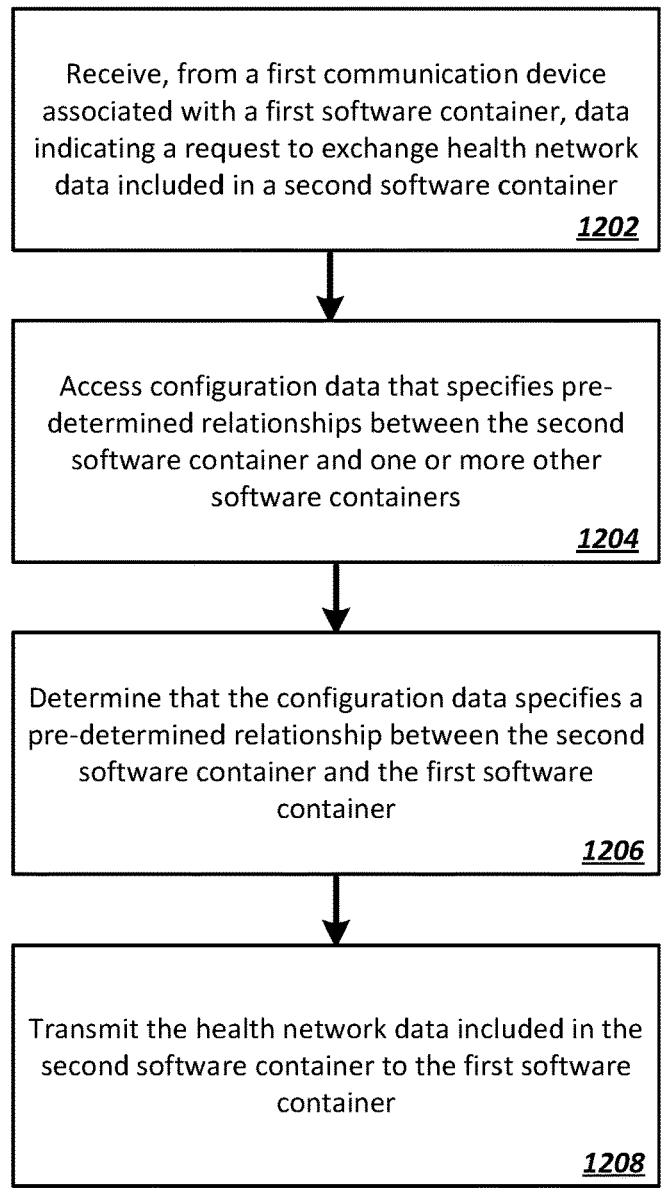
FIG. 12 is a process performed by a system that can provide a zero-knowledge environment for health networking based on containers.

FIG. 12 is a process 1200 performed by a system that can provide a zero-knowledge environment for health networking based on containers. For example, the process 1200 can be performed by the system 300 of FIG. 3, or another system that is capable of providing a zero-knowledge environment using a software container architecture. Similarly to as described above in regards to users of social network in process 1100, the process 1200 may be used in the context of users interacting with a network of healthcare providers and support stakeholders, which can be referred to as a health network. A user's health network can include but is not limited to their healthcare providers, insurance payers, caregivers, and family. Healthcare providers can include, but are not limited to, hospitals, primary care, specialist care, chronic care, lab testing, dentists, and pharmacies. The data collected from interacting with their healthcare network can be referred to as the Healthcare Identity Graph. This data can include many different advantageous aspects of a user's interaction with their healthcare network. All Healthcare Identity Graph data can be generically referred to as user health data or health network data.

Data elements of the Healthcare Identity Graph can include various types of events, including but not limited to a visit event, discharge event, transfer event, share event, request event, receive event, care plan event, payment event, reimbursement event, publish event, subscribe event, and decision event. Data elements can also include information about the structure of their healthcare network.

Some users of the health network may correspond with patients, other users may correspond with stakeholders for health network data such as physicians, family caregivers, and other care providers that use health network data to better provide care to the patient, and social networks may correspond to health networks. Health network data of a patient may include electronic medical records that describe a patient's name, gender, age, height, weight, medical history, x-ray scans, doctor visits, and other health related information related to the patient. Health network data may also include any type of Protected Health Information (PHI), as defined by the Health Insurance Portability and Accountability Act of 1996 (HIPAA), that is generated by the health network or otherwise in the patient's interaction within their health network. A patient may specify health network data to provide to different health networks, and for each health network, further specify health network data provided to the health network to provide to particular stakeholders. For example, patient may specify that a health network only has access to a limited set of health information regarding the patient, and further specify that a particular doctor may only have access to only a subset of the limited set of health information through the health network.

The system can receive, from a first communication device associated with a first software container related to a first user identity, data indicating a request to exchange health network data included in a second software container related to a second user identity (1202). For example, the system 300 can receive data indicating a request to exchange health network data from a communication device that is associated with the software container 320 related to the user A, e.g., a doctor. The request can be one to receive health network data included in the software container 340 related to the user B, e.g., a patient of the doctor. Exchange may refer to a one way data exchange. For example, an exchange of information between a container of a doctor and a container of a patient may include only providing health network data from the container of the patient to the container of the doctor.

As described, each of the first software container and the second software container can be an independent server virtualization instance that is configured to operate independently of other processes operating on a same processing resource as the independent server virtualization instance. The request to exchange health network data can comprise at least a first network address that uniquely identifies the first software container and a second network address uniquely identifying the second software container.

In some implementations, the data indicating the request can be received by an application instance operating on a communication device associated with the user A, such as an application associated with the system 300, e.g., a health network application for a zero-knowledge health network. Alternatively, the data indicating the request can be received by the controller 328 of the container 320. The data indicating the request can also include information identifying the first and second software containers, where such information may be first and second network addresses that each uniquely identify a single software container. Such network addresses may be, for example, IPv6 or DNS addresses. In some instances, the first and second software containers can exist on users' communication devices. For example, the first software container may be hosted on the first communication device, and the second software container may be hosted on a second communication device. The communication devices may be those of the users to whom the user identities correspond. For example, user A may have a first user identity, and the container 320 associated with the first user identity may belong to the user A. Similarly, user B may have a user identity, and the container 340 associated with the second user identity may belong to the user B. Alternatively, the containers 320, 340 may be hosted remotely from the communication devices, e.g., at a cloud service, and in such cases the data indicating the request may be received by the system, e.g., a health network system, from a communication device over one or more networks, and/or may be received by the controller 328 of the container 320 that is hosted in the cloud over one or more networks.

The system can access configuration data that specifies pre-determined relationships between the second software container and one or more other software containers (1204). Each of the pre-determined relationships specified by the configuration data can permit health network data to be exchanged between the second software container and the one or more other software containers. Additionally, each of the pre-determined relationships between the second software container and the one or more other software containers can be specified by a second communication device that is associated with the second software container.

For example, the container 340 relating to the user B can store configuration data locally in the container 340, or configuration data relating to the container 340 can be stored externally to the container 340 in the system 300, for example, such that the configuration data is accessible at the directory server 310 or at another server associated with the system 300. The configuration data may include pre-determined relationships, that is, relationships between the second container 340 and other containers, where a relationship enables information to be exchanged between the containers. In some implementations, the only device that may be able to modify the configuration data associated with the second container 340 may be the communication device that is associated with the container 340, thereby giving the user B exclusive control over the relationships between their container 340 and other containers. Such control allows the user B to completely control how information in their container 340 is shared with other users and entities of the zero-knowledge health network.

In some implementations, the configuration data may include additional information in relation to the pre-determined relationships, such as security levels associated with the pre-determined relationship that govern which health network data may be provided to other containers, thereby giving the user further control over how information in their container is shared within the health network. In some implementations, a pre-determined relationship between two containers may be a publish-and-subscribe relationship, such that a container may be indicated as only publishing information to one or more other containers, only subscribing to information that has been published in one or more other containers, or both publishing and subscribing to information that is in other containers. This provides additional control to a user, in that they may control who sees which information in their container, as well as what information they receive, e.g., from other containers, from advertising entities, and so on.

The system determines that the configuration data specifies a pre-determined relationship between the second software container and the first software container that permits health network data to be exchanged between the second software container and the first software container (1206). For example, the system can inspect the accessed configuration data and determine that a pre-determined relationship between the first and second software containers is specified by the configuration data. The system may further determine that the pre-determined relationship between the first and second software containers permits the health network data included in the second software container to be exchanged with the first software container, that is, such that the health network data in the second software container may be provided to the second software container such that the health network data in the second software container can be presented for output at the first communication device associated with the first software container.

For instance, the controller 348, an application associated with the system 300, or another component of the system 300 may inspect the configuration data associated with the second container 340 that is stored at the second container 340 or elsewhere in the system 300, and may determine that the configuration data specifies a pre-determined relationship between the two software containers 320, 340. The configuration data may further specify that the pre-determined relationship between the two software containers 320, 340 enables the health network data, e.g., the data subset P associated with user B's health network data 343, to be exchanged with the first software container 320.

Determining that the health network data can be exchanged with the first software container 320 may include determining that the health network data is identified as having been published. For example, the user B can indicate when to publish health network data that is included in their container 340, such that the health network information is only provided to the container 320 if it has been published by the user B. Such a feature ensures that only the health network data that user B wants to share in the health network will be shared, and that other users or entities associated with the health network cannot access this health network data until it has been published. In some implementations, a default setting for the publish-and-subscribe system may be that health network data is automatically published, such that subscribers can access the health network data once it has been added by the user B and stored in the second container 340.

Based on determining that the configuration data specifies a pre-determined relationship between the second software container and the first software container that permits health network data to be exchanged between the second software container and the first software container, the health network data included in the second software container is transmitted to the first software container (1208). For example, based on determining that the configuration data associated with the second software container includes a pre-determined relationship between the second software container and the first software container, and determining that the pre-determined relationship permits the health network data to be transmitted to the first software container, the health network data, e.g., a copy or a pointer to the data, can be transmitted to the first software container. Based on receiving the transmission including the health network data included in the second software container, the first communication device associated with the first software container may provide the received health network data for output at the first communication device.

For example, based on determining that the data set P associated with user B's first health network data 343 that is stored in the container 340 can be exchanged with the container 320, a copy or pointer to the data set P can be transmitted to the container 320. In some implementations, the decision to transmit the health network data to the container 320 can be made by the controller 348 of the container 340, and the transmission of the health network data can be received by the controller 328 of the container 320. In response to receiving the transmission, the system 300, e.g., the controller 328 or an application instance operating on the first communication device associated with the container 320, can also present the received health network data for output at the first communication device. For example, based on receiving health network data corresponding to health network data of the second user identity related to the second container 340, the first communication device associated with the container 320 can provide the health network data of the second user identity for output at a display of the first communication device. In some implementations, the system 300 may store the received health network data at the first software container 320. In other implementations, the health network data transmitted from the second software container 340 may be received through the system 300 by an application instance operating on the first communication device, such that the first communication device can present the health network data included in the second container 340 without needing to access the health network data at the first software container 320. In some implementations, the health network data may be provided to the application instance on the first client device for output without the health network data being provided to the first software container. This effectively would allow a user, such as user A, of the first communication device associated with the first software container 320, to view the health network data included in the second software container 340 without such information being transmitted to another software container.

Similar processes may also be used by a communication device to obtain permission to add health network information to a container. For example, a user of the second communication device and having the second user identity may wish to add information to a health network profile that is stored in the second software container that is related to the second user identity. To permit the user to add the information to the health network profile, the system can perform a process. Such a process may include receiving, from the second communication device, data indicating a request for the second network address that uniquely identifies the second software container, wherein the request includes health network authorization information corresponding to the second user identity. The system can then authorize the second communication device to add health network data relating to the second user identity to the second software container based at least on the health network authorization information corresponding to the second user identity. Based on authorizing the second communication device to add health network data relating to the second user identity to the second software container, the system transmits, to the second communication device, information indicating the second network address uniquely identifying the second software container. The system then receives from the second communication device, health network data and information specifying the second network address uniquely identifying the second software container. The health network data received from the second communication device is then stored in the second software container, as the health network data included in the second software container discussed in conjunction with the process 1200, based at least on authorizing the second communication device to add health network data relating to the second user identity to the second software container and receiving the information specifying the second network address uniquely identifying the second software container. Relying on the system of FIG. 3, for example, the user B may be using a communication device that is in communication with the system 300, and may submit a request to add first health network data to the container 340 that is related to user B's first health network account. User B can include, with their request, health network authorization information, such as a username and password, that can be received by the system 300, e.g., at the directory server 310, the controller 348 of the container 340, or another component of the system 300. The username and password submitted by user B can be verified such that the communication device being used by user B is authorized, e.g., to add health network data to user B's first health network account. To enable the authorized communication device to add information to the software container 340, the system 300 can provide the communication device with the network address that uniquely identifies the second software container 340, e.g., the appropriate IPv6 or DNS address. The system 300 can subsequently receive health network data from the authorized communication device, wherein the health network data can be associated with information specifying the network address that uniquely identifies the second software container 340. The received health network data can be stored at the second software container 340 based on the received health network data being received along with information that specifies the network address that uniquely identifies the second software container 340.

In some implementations, the system may utilize a publish-and-subscribe system to exchange information between software containers. In such a case, the process 1100 of FIG. 11 may include additional steps for determining whether the health network data can be transmitted to the first software container. For example, the process may include determining, based on the configuration data, that the health network data included in the second software container is included among published health network data included in the second software container, wherein including health network data among published health network data enables corresponding subscribers to the published health network data to access the published health network data. The process may further include determining, based on accessing second configuration data that specifies pre-determined relationships between the first software container and one or more other software containers, wherein each pre-determined relationship between the first software container and one or more other software containers is specified by the first communication device and permits health network data to be exchanged between the first software container and the one or more other software containers, that the first user identity is a subscriber to the published health network data included in the second software container. Finally, the system can transmit the health network data included in the second software container to the first software container based on determining that the health network data included in the second software container is included among published health network data included in the second software container, and determining that the first user identity is a subscriber to the published health network data included in the second software container.

Additionally, in some implementations, each of the first software container and the second software container is associated with controls that permit access to data stored at the software container according to privacy rules. Such controls may enable a health network or other service maintaining such software containers to comply with domestic, local, or international privacy regulations.

Additionally, in some implementations, the second software container includes health network data relating to two or more different health networks. Thus, as shown in FIG. 3, each of the containers 320, 340 can include health network information for multiple health networks that all relate to the same individual user, e.g., a first hospital network, a second hospital network, a vision provider network, and other health network accounts that all relate to the same user B.

As discussed, in implementations of the zero-knowledge system discussed, the data indicating the request to exchange the health network data is received from a health network application instance operating on the first communication device, wherein the health network application instance is associated with the health network engine. Such health network applications enable fairly small applications to operate on individual users' communication devices that enable the users to interact with the containers of the zero-knowledge health network; e.g., to view information being exchanged in the health network. Such an application may permit, as an addition to the process 1200, providing the health network data included in the second software container for output at a display of the first communication device.

As discussed previously with respect to the network addresses that uniquely identify the software containers of the process 1200, the first network address uniquely identifying the first software container may be a first IPv6 or DNS address that points to the first software container and that does not point to any additional software containers, and the second network address uniquely identifying the second software container may be a second IPv6 or DNS address that points to the second software container and that does not point to any additional software containers.

Additionally, to provide added security in the exchange of information between containers in the system, transmitting the health network data included in the second software container to the first software container may comprise encrypting the health network data before transmission and decrypting the encrypted health network data upon receipt. For example, the transmission process may include encrypting the health network data using a public encryption key that is included in the second software container, transmitting the encrypted health network data to the first software container, and decrypting the encrypted health network data using a private encryption key that is included in the first software container.

Moreover, to provide for added control of the user over the information included in their container and how that information is shared, the configuration data discussed with respect to the process 1200 may be included in the second software container.

Figure 13:
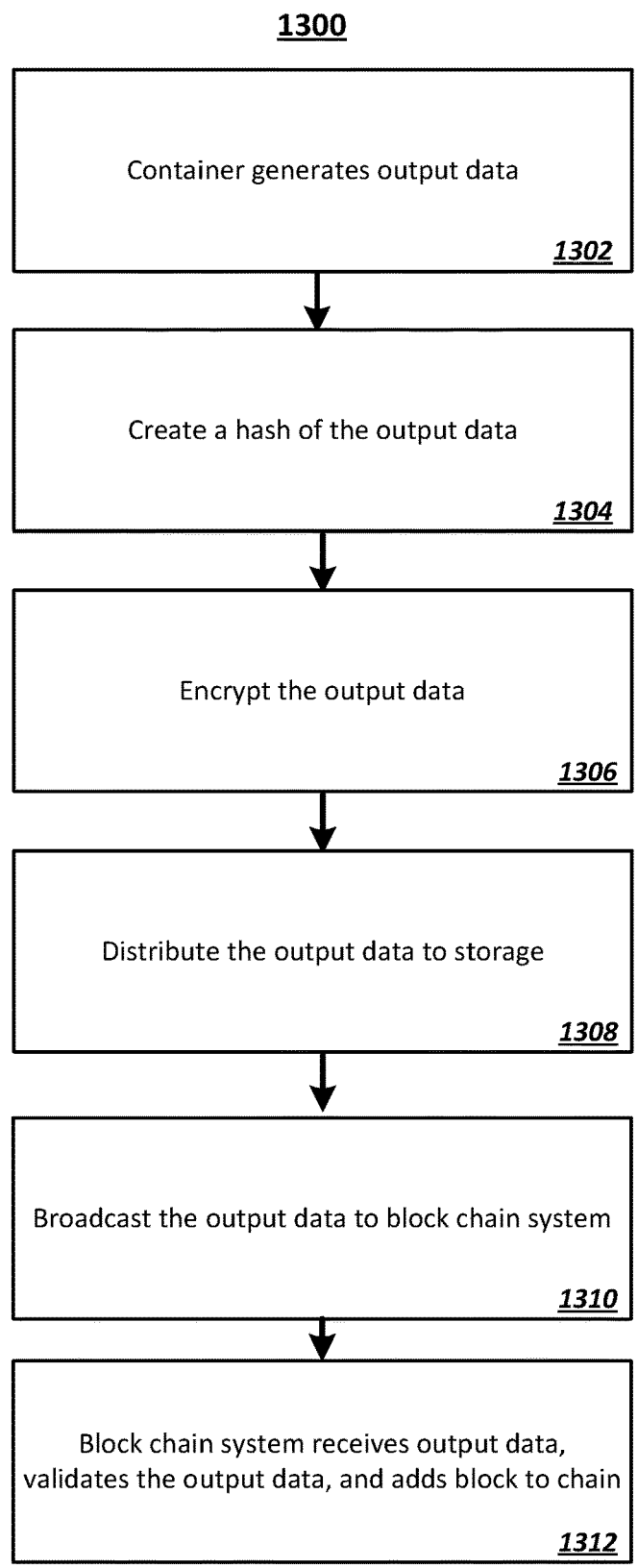
FIG. 13 is a process performed by a system that can provide recording data output by a container to validate the authenticity of the output data.

FIG. 13 is a process 1300 performed by a system that can provide recording data output by a container to validate the authenticity of the output data. Capturing the history of healthcare related output, such as outcome data and action data, with the ability to validate the authenticity of this output for non-repudiation purposes can be referred to as authenticity data or Healthcare Liability Graph data. A Healthcare Liability Graph will become critically important as healthcare stakeholders, such as providers and payers, become increasingly inundated with healthcare related data. In this environment, healthcare stakeholders will be severely challenged in making potentially life dependent decisions on data that can't be validated as authentic. And once these decisions are made, these healthcare stakeholders need the ability to establish a verifiable history for the data during potential legal proceedings. The health network data used in the above description of FIG. 12 may include the Healthcare Liability Graph data. All Healthcare Liability Graph data can be generically referred to as user health data.

Similar to the Healthcare Identity Graph, data stored in the Healthcare Liability Graph, such as events, decisions, etc., may be stored as nodes of the graph connected by edges representing relationships between the events, decisions, etc. In other implementations, the events, decisions, etc. of the Healthcare Liability Graph may be stored in a linked list structure, in a relational database, or using another data structure.

Containers may be used to achieve an output (1302). As previously described, the containers can be hosted on user devices or a server. For example, application code in a container can be used to achieve any healthcare related output including but not limited to diagnosing patients, identifying health risks, conducting transactions, determining decisions, capturing events, calculating priorities, calculating scores, splitting network data into fragments, aggregating fragments, etc. In some implementations, the container of a health care provider may send a rule set to a container of a patient for the container of the patient to then use to analyze health network data as part of a population health service and generate output data to provide the container of the health care provider. A rule set can be set of instructions, application code, algorithms, or any combination that defines and directs the analysis of the health network data. In an exemplary embodiment, algorithms are used to calculate specific output data. Output data can be defined as any data that is the result of processing an algorithm or performing any type of calculation. Algorithms can include but are not limited to calculating scores, priorities, events, decisions, actions, care plans, profile data, and outcome probability. All output data can be referred to as user health data or health network data.

This approach of using containers is critically different than current population health analytics services and companies operating today where sensitive health data is shared and potentially at risk of being exposed. In contrast, the approach of using containers to store sensitive health network data is more secure and private since this data is not shared or otherwise exposed to any services or companies. In a container approach the population health company creates a rule set A hash is created that is related to the output data (1304). This can be referred to as the output hash. For the purposes of this description, a hash is a general term for confirming the validity of the origin of the output data and validating the integrity of the output data, and can be accomplished via a number of advantageous means, some of which are previously described. A hash of this output data can be referred to as a type of authentication information. In an exemplary embodiment, the output hash can be generated based on the output data, such as a file or text string that is an output of executing the application code. In an exemplary embodiment, the output hash can be generated based on the related container data that generated the output data. The container data used for the output hash can include, but is not limited to, the payload data of the container, such as the application, libraries, other binaries, and configuration files, and any other advantageous container-related data. In an exemplary embodiment, the output hash can be generated based on the time, date, and location of the execution of the output data. The location can include, but is not limited to, the location of the user device. In an exemplary embodiment, the output hash is created based on the output data, the container data, the time, date and location data, and the container signature, or any combination thereof.

The output data is encrypted (1306). In an exemplary embodiment, the output data can be encrypted using the hash as the public key. In an exemplary embodiment, the hash can be used as an identifier for the output data. This type of identifier is advantageous since it is not associated with the user, thereby increasing the anonymity and security of the output data.

The output data is distributed to storage (1308). The storage of the output data can include but is not limited to local storage, hosted storage, electronic medical record storage systems, cloud storage services, P2P storage networks, or any combination of these, or other advantageous storage mechanisms. In an exemplary embodiment, multiple copies of the output data can be stored to ensure redundancy, such that an inaccessible storage location cannot prevent the aggregation of the electronic medical record. The algorithm for determining the number of output data copies to store can include but is not limited to the previously described Shamir's (k, n) threshold scheme, RAID, or other advantageous data redundancy approaches. The data of each output data storage location is then recorded and stored. In an exemplary embodiment, this output data storage location data can be stored in an address server as previously described. In an exemplary embodiment, this output data storage location data can be encrypted. In an exemplary embodiment, the output data storage location data can be encrypted using its identifier as the public key. The output data storage location data identifier can be a hash based on the payload data and/or the container data.

In an exemplary embodiment, the container of a user can be the only source of the output data locations. This adds a level of security since only the user who is authenticated to access the container of the user has the information to locate the output data.

The relevant output data is broadcast to the block chain system (1310). In an example, the address server can broadcast the output data to a block chain system. The block chain system may include multiple servers.

The block chain system receives the output data that is broadcast, validates the output data, and then posts the output data into a new block of transactions (1312). In an example, the process to validate and post output data can emulate the process used for bitcoin transactions, as described by Bitcoin, "Transactions." Oct. 20, 2016. Web. <https://bitcoin.org/en/developer-guide#transactions>

In some embodiments, the block chain data may capture transactions between two parties, and also data related to determining decisions, capturing events, calculating priorities, calculating scores, splitting network data into fragments and storing the fragmented network data, aggregating the fragmented network data, etc. In these embodiments, the block chain data is captured with only one identifier representing the user 120.

Recording the container output data in a block chain can be very advantageous for capturing the history of healthcare related processes for non-repudiation purposes. Such a Healthcare Liability Graph can help establish a chain of trust for all healthcare related output, effectively capturing an output history that can be utilized in legal proceedings, various analyses, and many other efforts to improve the quality of healthcare. A number of benefits can be realized by utilizing block change technology in the sharing network data including container output data. For example, authentication of the identities of both the user and a recipient can be improved using an address based on public and private key cryptography. In another example, the validity of the Healthcare Identity Graph data and electronic medical record data can be improved by capturing the history of all sharing transactions in a block chain. The recipient therefore can have more confidence that the Healthcare Identity Graph data and electronic medical record data is valid when the recipient can verify the chain of all sharing transactions from the data's origination. In another example, the privacy of the user can be enhanced by using a non-identifiable address for each sharing transaction. The Healthcare Identity Graph data and electronic medical record data will still include the identity of the user, but this data will be encrypted as part of the transaction.

While process 1300 describes output data from a container of a user being broadcast to a block chain system, in other processes the output data may not be broadcast to a block chain system. For example, another process may simply end with a container of a user distributing output data from the container to storage (1308) for later retrieval from storage.

In an exemplary embodiment, any data that is stored in the user device can be backed up using standard back up services provided by mobile services including but not limited to Apple, Android, Microsoft, Google and Samsung.

Figure 14:
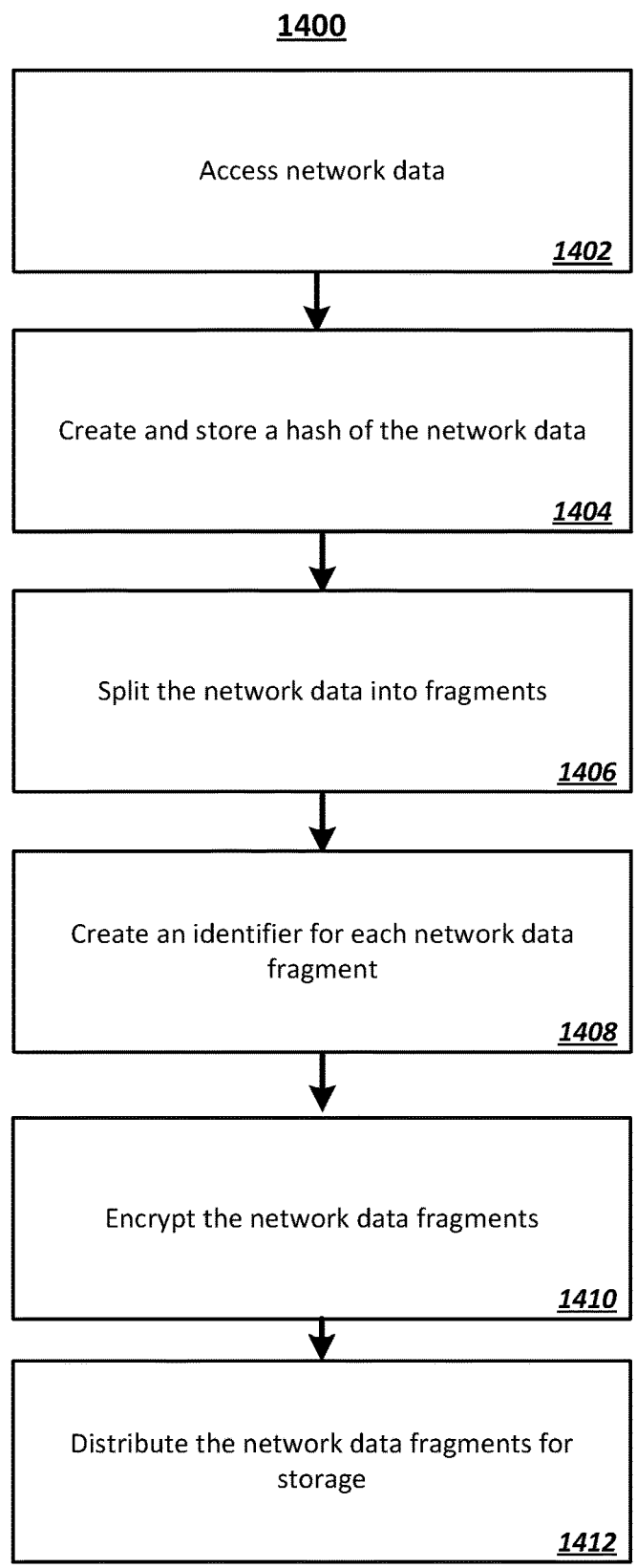
FIG. 14 is a process performed by a system that can provide splitting network data into fragments and storing the fragmented network data.

FIG. 14 is a process performed by a system that can provide splitting network data into fragments and storing the fragmented network data. The container accesses a complete set of network data, which may include a file or multiple files that describes social network data, health network data, or a combination (1402). For example, a container of a user hosted in a cloud may receive social network data captured by a user device of the user and uploaded by the user device to the container. In another example, a container of a user hosted locally on the user device may receive health network data obtained by the user device of the user.

In an exemplary embodiment, the container creates a hash of the network data (1404). The purpose of this hash is to be able to validate the network data after it has been aggregated from fragments in a later step. This hash can be stored with the network data in the container.

The container can split the network data file into fragments (1406). In an exemplary embodiment, the network data can be split using a (k, n) threshold scheme, as described by Shamir et al, "How to Share a Secret." Communications of the ACM, November 1979, Vol 22, Number 11, hereafter "Shamir" which is hereby incorporated by reference in its entirety. In an exemplary embodiment, the fragment size may be defined as a variable by the user. Such a fragment variable can be defined as a percentage of the file, a fragment size in bytes, or other advantageous means to define the fragment size. In an exemplary embodiment, the network data can be split using differential privacy technology, as described by Dwork. In other embodiments, any advantageous algorithms or other means can be used to split the network data into fragments. In an exemplary embodiment, any additional validation data, such as a digital certificate, a digital watermark, or electronic postmark can be stored with the fragments in order to retain the authenticity of the network data. This approach maintains the chain of trust when sharing the aggregated network data. The algorithm for splitting the network data into fragments stores the parameters and/or instructions for aggregating the complete network data from its fragments.

The container creates an identifier for each network data fragment (1408). As previously described, each fragment can be stored using an identifier tied to the user's identity. In an exemplary embodiment, a hash can be used as the identifier. In an exemplary embodiment, a hash can be generated based on the payload data of the fragment, as previously described. In an exemplary embodiment, a hash can be generated based on container data. The container data used for the hash can include, but is not limited to, the payload data of the container, such as the application, libraries, other binaries, and configuration files, the date and time, the physical location of the device running the container, the container signature, and any other advantageous container related data. In an exemplary embodiment, a hash is created based on both the payload data of the fragment and the container data. In an exemplary embodiment, this approach for creating an identifier can also be applied to the parameters and/or instructions for aggregating the complete network data.

The container encrypts each fragment with a one-time public-private key pair using the identifier as the public key (1410). In an exemplary embodiment, the parameters and/or instructions for aggregating the network data can be encrypted. In an exemplary embodiment, the parameters and/or instructions can be encrypted using its identifier as the public key.

The container distributes the network data fragments to storage (1412). The storage of the network data fragments can include but is not limited to local storage, hosted storage, electronic medical record storage, cloud storage services, P2P storage networks, any combination of these, or other advantageous storage mechanisms. In an exemplary embodiment, multiple copies of the network data fragments can be stored to ensure redundancy, such that inaccessible storage locations cannot prevent the aggregation of the network data. The algorithm for determining the number of fragment copies to store can include but is not limited to the previously described Shamir's (k, n) threshold scheme, RAID, or other advantageous data redundancy approaches. The data of each fragment storage location is then recorded and stored.

In an exemplary embodiment, this fragment storage location data can be stored in an address server as previously described. In an exemplary embodiment, this fragment storage location data can be encrypted. In an exemplary embodiment, the fragment storage location data can be encrypted using its identifier as the public key. The fragment storage location data identifier can be a hash based on the payload data and/or the container data.

In some implementations where a container of a user is on a user device, the container may determine the location of storage. In one example, user device may include an address server that determines and stores the addresses of the stored portions. The addresses of the stored portions may point to each individual storage locale where a particular portion of the network data fragments may be retrieved. In this example, the address may include a universal resource locator (URL), a stub, a hyperlink, or any exemplary location mechanism. In this example, the address information stored may include indirect address information. Specifically, the storage of certain portions of network data fragments may be determined by an address server. The address server may have assigned the storage of certain portions of network data fragments to one or more storage servers. The address server may have mapped the storage locations for each segment of the portions of the network data fragments. As disclosed herein, when the container on the user device or another container attempts to access portions of the network data fragments, the container of the user may obtain the address information and then provide that address information to the container that is attempting to access portions of the network data fragments. In an exemplary embodiment, the container on a user device can be the only source of the fragment locations. This adds a level of security since only the user who is authenticated to access the user device has the information to locate and aggregate the network data fragments. In another implementation where a container of a user is on a cloud, the system may have a directory server, for example directory server 310 of FIG. 3, perform the functions of the address server to determine and store locations for the network data fragments.

For sharing network data with a recipient, the container of the user can transmit fragment storage location data and parameter/instruction data securely with a public/private key exchange as described above so the recipient container can aggregate the fragments back into the network data.

FIG. 15 is a process 1500 performed by a system that can provide analyzing health network data. In an exemplary embodiment, first location data is received from a wireless device of a patient that indicates a location of the wireless device (1502). For example, information may be received by a container of a user on the user device indicating an estimated location of the user device of the user.

In an exemplary embodiment, second location data indicating locations of one or more other users is accessed by the wireless device (1504). For example, the container of the user on the user device may access information indicating the locations of one or more healthcare providers.

In an exemplary embodiment, the wireless device determines, based at least on a comparison of the location of the wireless device to the one or more locations of the other users, that the location of the user corresponds to a location of a particular other user (1506). For example, the container of the user on the user device may compare the location of the user device, e.g., coordinates or an address determined for the user device, to locations of the healthcare providers, e.g., to coordinates or addresses of the healthcare providers. Based on the comparison, the container of the user on the user device may determine that the user device is proximate, e.g., within a threshold distance of, a particular one of the healthcare providers.

In an exemplary embodiment, the wireless device calculates at least one of an updated score, priority, or outcome probability in response to determining that the location of the user corresponds to the geographical location of the particular user (1508). For example, in response to determining that the user device is proximate to a particular healthcare provider, a container on the user device may compare health network user profile of the user associated with the user device to a care plan, Healthcare Identity Graph data, or electronic medical record data, or other processing may be performed. As described above, one or more scores, priorities, or probabilities may be computed based on the analysis or other processes. In some implementations, the system may additionally or alternatively generate one or more events, generate or modify health network data of the user, or generate or modify care plan data for the patient in response to determining that the location of the patient corresponds to the location of the particular healthcare provider. For example, an event may be determined based on an analysis of Healthcare Identity Graph data, electronic medical record data, care plan data, patient profile data, or other data.

In an exemplary embodiment, the wireless device transmits, to a recipient container, at least one of an alert, network data regarding the user, or a recommendation based at least on the calculation of the at least one of the updated score, priority, or outcome probability (1510). Per previously disclosed embodiments, there are many types of network data, such as Healthcare Identity Graph data, electronic medical record data, output data, outcome data, and Healthcare Liability Graph data. Based on the one or more scores, probabilities, or priorities calculated, the container of the user on the user device or another component of the system may determine to provide an alert, a particular electronic medical record of the user, or a recommendation to a recipient container. The alerts, electronic medical records, or recommendations may include those disclosed previously using the methods disclosed elsewhere in the specification.

In an exemplary embodiment, the wireless device transmits authentication information for the at least one of the alert, the network data of the user, or the recommendation (1512). For example, the container of the user on the user device may transmit authentication information to the recipient container, the block chain system, or to another component of the system. As disclosed, the authentication information may be used to authenticate the alert, the network data, or the recommendation provided by the user device, to ensure that the alert, network data, or the recommendation is legitimate. The authentication information may be used, for example, in a Healthcare Liability Graph to indicate that the alert, network data, or recommendation is a legitimate one.

Implementations of the subject matter and the functional operations described in this specification can be implemented in digital electronic circuitry, in tangibly-embodied computer software or firmware, in computer hardware, including the structures disclosed in this specification and their structural equivalents, or in combinations of one or more of them. Implementations of the subject matter described in this specification can be implemented as one or more computer programs, i.e., one or more modules of computer program instructions encoded on a tangible non-transitory program carrier for execution by, or to control the operation of, data processing apparatus. Alternatively or in addition, the program instructions can be encoded on an artificially-generated propagated signal, e.g., a machine-generated electrical, optical, or electromagnetic signal that is generated to encode information for transmission to suitable receiver apparatus for execution by a data processing apparatus. The computer storage medium can be a machine-readable storage device, a machine-readable storage substrate, a random or serial access memory device, or a combination of one or more of them.

The term "data processing apparatus" refers to data processing hardware and encompasses all kinds of apparatus, devices, and machines for processing data, including by way of example a programmable processor, a computer, or multiple processors or computers. The apparatus can also be or further include special purpose logic circuitry, e.g., a central processing unit (CPU), a FPGA (field programmable gate array), or an ASIC (application-specific integrated circuit). In some implementations, the data processing apparatus and/or special purpose logic circuitry may be hardware-based and/or software-based. The apparatus can optionally include code that creates an execution environment for computer programs, e.g., code that constitutes processor firmware, a protocol stack, a database management system, an operating system, or a combination of one or more of them. The present disclosure contemplates the use of data processing apparatuses with or without conventional operating systems, for example Linux, UNIX, Windows, Mac OS, Android, iOS or any other suitable conventional operating system.

A computer program, which may also be referred to or described as a program, software, a software application, a module, a software module, a script, or code, can be written in any form of programming language, including compiled or interpreted languages, or declarative or procedural languages, and it can be deployed in any form, including as a stand-alone program or as a module, component, subroutine, or other unit suitable for use in a computing environment. A computer program may, but need not, correspond to a file in a file system. A program can be stored in a portion of a file that holds other programs or data, e.g., one or more scripts stored in a markup language document, in a single file dedicated to the program in question, or in multiple coordinated files, e.g., files that store one or more modules, sub-programs, or portions of code. A computer program can be deployed to be executed on one computer or on multiple computers that are located at one site or distributed across multiple sites and interconnected by a communication network. While portions of the programs illustrated in the various figures are shown as individual modules that implement the various features and functionality through various objects, methods, or other processes, the programs may instead include a number of sub-modules, third party services, components, libraries, and such, as appropriate. Conversely, the features and functionality of various components can be combined into single components as appropriate.

The processes and logic flows described in this specification can be performed by one or more programmable computers executing one or more computer programs to perform functions by operating on input data and generating output. The processes and logic flows can also be performed by, and apparatus can also be implemented as, special purpose logic circuitry, e.g., a central processing unit (CPU), a FPGA (field programmable gate array), or an ASIC (application-specific integrated circuit).

Computers suitable for the execution of a computer program include, by way of example, can be based on general or special purpose microprocessors or both, or any other kind of central processing unit. Generally, a central processing unit will receive instructions and data from a read-only memory or a random access memory or both. The essential elements of a computer are a central processing unit for performing or executing instructions and one or more memory devices for storing instructions and data. Generally, a computer will also include, or be operatively coupled to receive data from or transfer data to, or both, one or more mass storage devices for storing data, e.g., magnetic, magneto-optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device, e.g., a universal serial bus (USB) flash drive, to name just a few.

Computer-readable media (transitory or non-transitory, as appropriate) suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto-optical disks; and CD-ROM and DVD-ROM disks. The memory may store various objects or data, including caches, classes, frameworks, applications, backup data, jobs, web pages, web page templates, database tables, repositories storing business and/or dynamic information, and any other appropriate information including any parameters, variables, algorithms, instructions, rules, constraints, or references thereto. Additionally, the memory may include any other appropriate data, such as logs, policies, security or access data, reporting files, as well as others. The processor and the memory can be supplemented by, or incorporated in, special purpose logic circuitry.

To provide for interaction with a user, implementations of the subject matter described in this specification can be implemented on a computer having a display device, e.g., a CRT (cathode ray tube), LCD (liquid crystal display), or plasma monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's client device in response to requests received from the web browser.

The term "graphical user interface," or GUI, may be used in the singular or the plural to describe one or more graphical user interfaces and each of the displays of a particular graphical user interface. Therefore, a GUI may represent any graphical user interface, including but not limited to, a web browser, a touch screen, or a command line interface (CLI) that processes information and efficiently presents the information results to the user. In general, a GUI may include a plurality of user interface (UI) elements, some or all associated with a web browser, such as interactive fields, pull-down lists, and buttons operable by the business suite user. These and other UI elements may be related to or represent the functions of the web browser.

Implementations of the subject matter described in this specification can be implemented in a computing system that includes a back-end component, e.g., as a data server, or that includes a middleware component, e.g., an application server, or that includes a front-end component, e.g., a client computer having a graphical user interface or a Web browser through which a user can interact with an implementation of the subject matter described in this specification, or any combination of one or more such back-end, middleware, or front-end components. The components of the system can be interconnected by any form or medium of digital data communication, e.g., a communication network. Examples of communication networks include a local area network (LAN), a wide area network (WAN), e.g., the Internet, and a wireless local area network (WLAN).

Other implementations are within the scope of the following claims. For example, the same architecture can be used with or without security. If implemented with security, it allows ad hoc groups to be formed for confidentially sharing information and managing activity. This may be used for environments where confidentiality is required (e.g., a clean room being used to manage a pre-acquisition diligence) and national security teams (e.g., a tactical messaging infrastructure for deployed soldiers or strategic intelligence sharing).

The computing system can include clients and servers. A client and server are generally remote from each other and typically interact through a communication network. The relationship of client and server arises by virtue of computer programs running on the respective computers and having a client-server relationship to each other.

While this specification contains many specific implementation details, these should not be construed as limitations on the scope of any invention or on the scope of what may be claimed, but rather as descriptions of features that may be specific to particular implementations of particular inventions. Certain features that are described in this specification in the context of separate implementations can also be implemented in combination in a single implementation. Conversely, various features that are described in the context of a single implementation can also be implemented in multiple implementations separately or in any suitable sub-combination. Moreover, although features may be described above as acting in certain combinations and even initially claimed as such, one or more features from a claimed combination can in some cases be excised from the combination, and the claimed combination may be directed to a sub-combination or variation of a sub-combination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the implementations described above should not be understood as requiring such separation in all implementations, and it should be understood that the described program components and systems can generally be integrated together in a single software product or packaged into multiple software products.

Particular implementations of the subject matter have been described. Other implementations, alterations, and permutations of the described implementations are within the scope of the following claims as will be apparent to those skilled in the art. For example, the actions recited in the claims can be performed in a different order and still achieve desirable results.

Accordingly, the above description of example implementations does not define or constrain this disclosure. Other changes, substitutions, and alterations are also possible without departing from the spirit and scope of this disclosure.

What is claimed is:

1. A computer-implemented method performed by a network engine comprising:
receiving, at a first software container related to a user on a user device, first geographic location data indicating a geographic location of the user device, wherein the first software container is an independent server virtualization instance that is configured to operate independently of other processes operating on a same processing resource as the independent server virtualization instance, and operates to store health network data related to the user, and to facilitate encrypted communications between the user device and one or more electronic devices;
accessing, with an application instance installed at the first software container on the user device, second geographic location data indicating one or more geographic locations of one or more healthcare providers;
determining, with the application instance installed at the first software container on the user device, that the geographic location of the user corresponds to a geographic location of a particular healthcare provider, at least in part, by comparing the geographic location of the user device to the one or more geographic locations of the one or more healthcare providers, and determining that the user device is within a threshold distance of the particular healthcare provider;
in response to determining that the geographic location of the user corresponds to the geographic location of the particular healthcare provider, determining, with the application instance installed at the first software container on the user device, at least one of an updated score, a priority, or an outcome probability;
encrypting, at least one of an alert, the health network data related to the user, or a recommendation using a public encryption key that is included in the first software container;
in response to determining the at least one of the updated score, the priority, or the outcome probability, transmitting, from the first software container on the user device to a recipient software container, the encrypted at least one of the alert, the health network data related to the user, or the recommendation, wherein the recipient software container is an independent server virtualization instance that is configured to operate independently of other processes operating on a same processing resource as the independent server virtualization instance;
decrypting the encrypted at least one of the alert, the health network data related to the user, or the recommendation using a private encryption key that is included in the recipient software container; and
transmitting, from the first software container on the user device to the recipient software container, authentication information for the at least one of the alert, the health network data related to the user, or the recommendation, wherein the authentication information permits the recipient software container to confirm authenticity of the at least one of the alert, the health network data related to the user, or the recommendation.

2. The computer-implemented method of claim 1, wherein each of the first software container and the recipient software container is associated with controls that permit access to data stored at the software container according to privacy rules.

3. The computer-implemented method of claim 1, wherein the first software container includes health network data relating to two or more different health networks.

4. The computer-implemented method of claim 1, wherein the health network data related to the user includes at least one of Healthcare Identity Graph data, electronic medical record data, output data, outcome data, or Healthcare Liability Graph data.

5. The computer-implemented method of claim 1, comprising:
receiving, at the first software container from the recipient software container, a rule set for generating output data based on the health network data relating to the user;
generating, by the first software container, the output data according to the rule set and the health network data relating to the user; and
providing, by the first software container, the output data to the recipient software container.

6. The computer-implemented method of claim 1, comprising:
generating, by the first software container, output data from the health network data;
distributing, by the first software container, the output data to storage; and
broadcasting, by the first software container, the output data to a block chain system.

7. The computer-implemented method of claim 1, comprising:
fragmenting the health network data related to the user into a plurality of health network data fragments;
encrypting each of the plurality of health network data fragments;
storing the plurality of encrypted health network data fragments; and
providing the recipient software container access to the stored encrypted plurality of health network data fragments.

8. The computer-implemented method of claim 1, wherein comparing the geographic location of the user device to the geographic locations of the one or more healthcare providers comprises comparing at least one of coordinates or an address determined for the user device to at least one of coordinates or addresses of the one or more healthcare providers.

9. A system comprising:
one or more computers and one or more storage devices storing instructions that are operable, when executed by the one or more computers, to cause the one or more computers to perform operations comprising:
receiving, at a first software container related to a user on a user device, first geographic location data indicating a geographic location of the user device, wherein the first software container is an independent server virtualization instance that is configured to operate independently of other processes operating on a same processing resource as the independent server virtualization instance, and operates to store health network data related to the user, and to facilitate encrypted communications between the user device and one or more electronic devices;
accessing, with an application instance installed at the first software container on the user device, second geographic location data indicating one or more geographic locations of one or more healthcare providers;
determining, with the application instance installed at the first software container on the user device, that the geographic location of the user corresponds to a geographic location of a particular healthcare provider, at least in part, by comparing the geographic location of the user device to the one or more geographic locations of the one or more healthcare providers, and determining that the user device is within a threshold distance of the particular healthcare provider;
in response to determining that the geographic location of the user corresponds to the geographic location of the particular healthcare provider, determining, with the application instance installed at the first software container on the user device, at least one of an updated score, a priority, or an outcome;
encrypting at least one of an alert, the health network data related to the user, or a recommendation using a public encryption key that is included in the first software container;
in response to determining the at least one of the updated score, the priority, or the outcome probability, transmitting, from the first software container on the user device to a recipient software container, the encrypted at least one of the alert, the health network data related to the user, or the recommendation, wherein the recipient software container is an independent server virtualization instance that is configured to operate independently of other processes operating on a same processing resource as the independent server virtualization instance;
decrypting the encrypted at least one of the alert, the health network data related to the user, or the recommendation using a private encryption key that is included in the recipient software container; and
transmitting, from the first software container on the user device to the recipient software container, authentication information for the at least one of the alert, the health network data related to the user, or the recommendation, wherein the authentication information permits the recipient software container to confirm authenticity of the at least one of the alert, the health network data related to the user, or the recommendation.

10. The system of claim 9, wherein each of the first software container and the recipient software container is associated with controls that permit access to data stored at the software container according to privacy rules.

11. The system of claim 10, wherein the first software container includes health network data relating to two or more different health networks.

12. The system of claim 9, wherein the health network data related to the user includes at least one of Healthcare Identity Graph data, electronic medical record data, output data, outcome data, or Healthcare Liability Graph data.

13. The system of claim 9, comprising:
receiving, at the first software container from the recipient software container, a rule set for generating output data based on the health network data relating to the user;
generating, by the first software container, the output data according to the rule set and the health network data relating to the user; and
providing, by the first software container, the output data to the recipient software container.

14. The system of claim 9, comprising:
generating, by the first software container, output data from the health network data;
distributing, by the first software container, the output data to storage; and
broadcasting, by the first software container, the output data to a block chain system.

15. The system of claim 9, comprising:
fragmenting the health network data related to the user into a plurality of health network data fragments;
encrypting each of the plurality of health network data fragments;

storing the plurality of encrypted health network data fragments; and providing the recipient software container access to the stored encrypted plurality of health network data fragments.

16. The system of claim 9, wherein comparing the geographic location of the user device to the geographic locations of the one or more healthcare providers comprises comparing at least one of coordinates or an address determined for the user device to at least one of coordinates or addresses of the one or more healthcare providers.

17. A non-transitory computer-readable storage medium comprising instructions that, when executed by one or more computers, cause the one or more computers to perform operations comprising:

receiving, at a first software container related to a user on a user device, first geographic location data indicating a geographic location of the user device, wherein the first software container is an independent server virtualization instance that is configured to operate independently of other processes operating on a same processing resource as the independent server virtualization instance, and operates to store health network data related to the user, and to facilitate encrypted communications between the user device and one or more electronic devices;

accessing, with an application instance installed at the first software container on the user device, second geographic location data indicating one or more geographic locations of one or more healthcare providers;

determining, with the application instance installed at the first software container on the user device, that the geographic location of the user corresponds to a geographic location of a particular healthcare provider, at least in part, by comparing the geographic location of the user device to the one or more geographic locations of the one or more healthcare providers, and determining that the user device is within a threshold distance of the particular healthcare provider;

in response to determining that the geographic location of the user corresponds to the geographic location of the particular healthcare provider, determining, with the application instance installed at the first software container on the user device, at least one of an updated score, a priority, or an outcome;

encrypting, at least one of an alert, the health network data related to the user, or a recommendation using a public encryption key that is included in the first software container;

in response to determining the at least one of the updated score, the priority, or the outcome probability, transmitting, from the first software container on the user device to a recipient software container, the encrypted at least one of the alert, the health network data related to the user, or the recommendation, wherein the recipient software container is an independent server virtualization instance that is configured to operate independently of other processes operating on a same processing resource as the independent server virtualization instance;

decrypting the encrypted at least one of the alert, the health network data related to the user, or the recommendation using a private encryption key that is included in the recipient software container; and transmitting, from the first software container on the user device to the recipient software container, authentication information for the at least one of the alert, the health network data related to the user, or the recommendation, wherein the authentication information permits the recipient software container to confirm authenticity of the at least one of the alert, the health network data related to the user, or the recommendation.

18. The non-transitory computer-readable storage medium of claim 17, wherein comparing the geographic location of the user device to the geographic locations of the one or more healthcare providers comprises comparing at least one of coordinates or an address determined for the user device to at least one of coordinates or addresses of the one or more healthcare providers.

* * * * *

UNITED STATES PATENT AND TRADEMARK OFFICE
CERTIFICATE OF CORRECTION

PATENT NO. : 10,601,960 B2
APPLICATION NO. : 15/896347
DATED : March 24, 2020
INVENTOR(S) : William J. Raduchel and Art Spivy It is certified that error appears in the above-identified patent and that said Letters Patent is hereby corrected as shown below:

In the Claims

Column 40, Line 39, Claim 11, please delete "claim 10" and insert therefor -- claim 9 --

Signed and Sealed this
Second Day of June, 2020

Andrei Iancu
*Director of the United States Patent and Trademark Office*